(12) United States Patent
Li et al.

(10) Patent No.: US 9,392,786 B2
(45) Date of Patent: Jul. 19, 2016

(54) MECTIN AND MILBEMYCIN POLYELECTROLYTE NANOPARTICLE FORMULATIONS

(71) Applicant: Vive Crop Protection Inc., Toronto (CA)

(72) Inventors: Fugang Li, Richmond Hill (CA); Hung Hoang Pham, Brampton (CA); Darren J. Anderson, Toronto (CA)

(73) Assignee: Vive Crop Protection, Inc., Toronto (CA)

( * ) Notice: Subject to any disclaimer, the term of this patent is extended or adjusted under 35 U.S.C. 154(b) by 0 days.

(21) Appl. No.: 14/765,882

(22) PCT Filed: Feb. 5, 2014

(86) PCT No.: PCT/IB2014/058816
§ 371 (c)(1),
(2) Date: Aug. 5, 2015

(87) PCT Pub. No.: WO2014/122598
PCT Pub. Date: Aug. 14, 2014

(65) Prior Publication Data
US 2015/0366186 A1    Dec. 24, 2015

Related U.S. Application Data

(60) Provisional application No. 61/760,902, filed on Feb. 5, 2013.

(51) Int. Cl.
*A01N 25/00* (2006.01)
*A01N 25/12* (2006.01)
(Continued)

(52) U.S. Cl.
CPC ................ *A01N 25/12* (2013.01); *A01N 25/00* (2013.01); *A01N 25/04* (2013.01); *A01N 25/14* (2013.01); *A01N 43/90* (2013.01); *A01N 63/02* (2013.01)

(58) Field of Classification Search
CPC ....... A01N 25/00; A01N 25/12; A01N 25/14; A01N 43/90
See application file for complete search history.

(56) References Cited

U.S. PATENT DOCUMENTS 5,292,828 A    3/1994 Jenkins et al.
6,383,500 B1   5/2002 Wooley et al.
(Continued)

FOREIGN PATENT DOCUMENTS

CA    2203686 A1    11/1997
CA    2793082 A1    9/2011
(Continued)

OTHER PUBLICATIONS

International Search Report for PCT/IB2014/058816, 3 pages (May 28, 2014).
(Continued)

*Primary Examiner* — Carlos Azpuru
(74) *Attorney, Agent, or Firm* — Choate, Hall & Stewart LLP; Charles E. Lyon

(57) ABSTRACT

The present disclosure describes a formulation including a nanoparticle including a polymer-associated mectin and/or milbemycin compounds with an average diameter of between about 1 nm and about 500 nm; wherein the polymer is a polyelectrolyte, and a dispersant or a wetting agent. The disclosure describes various formulations and formulating agents that can be included in the formulations. Additionally, the disclosure describes application to various plants and pests as well as advantages of the disclosed formulations.

11 Claims, 3 Drawing Sheets

| Formulation | Type of Polymer in Nanoparticles | A.I. to Particle Weight Ratio | Target Abamectin Content | Measured Abamectin Content |
|---|---|---|---|---|
| Example 3 | S-MAA-NaAMPS | 5:1 | 10.0 | 10.0 |
| Example 4 | MAA-co-S | 1:1 | 2.0 | 1.8 |
| Example 5 | MAA-co-S | 1:1 | 4.1 | 3.5 |
| Example 6 | MAA-co-S | 1:2 | 2.1 | 1.8 |
| Example 7 | S-MAA-NaAMPS | 1:1 | 4.0 | 4.0 |
| Example 8 | S-MAA-NaAMPS | 1:2 | 4.0 | 3.6 |
| Example 9 | S-MAA-NaAMPS | 1:1 | 2.1 | 2.0 |

(51) Int. Cl.
*A01N 43/90* (2006.01)
*A01N 25/04* (2006.01)
*A01N 63/02* (2006.01)
*A01N 25/14* (2006.01)

(56) References Cited

U.S. PATENT DOCUMENTS

| | | |
|---|---|---|
| 6,383,984 B1 | 5/2002 | Aven |
| 6,436,421 B1 | 8/2002 | Schindler et al. |
| 6,604,698 B2 | 8/2003 | Verhoff et al. |
| 6,616,946 B1 | 9/2003 | Meier et al. |
| 6,683,129 B1 | 1/2004 | Eknoian |
| 6,897,253 B2 | 5/2005 | Schmucker-Castner et al. |
| 6,916,481 B1 | 7/2005 | Prud'Homme et al. |
| 7,070,795 B1 | 7/2006 | Botts et al. |
| 7,189,279 B2 | 3/2007 | Guillet |
| 7,939,601 B1 | 5/2011 | Bergeron et al. |
| 7,994,227 B2 | 8/2011 | Koltzenburg et al. |
| 8,029,827 B2 | 10/2011 | Martin |
| 8,034,888 B2 | 10/2011 | Nguyen-Kim et al. |
| 8,309,489 B2 | 11/2012 | Roldan Cuenya et al. |
| 8,372,418 B2 | 2/2013 | Dujardin et al. |
| 8,974,806 B2 | 3/2015 | Amrhein et al. |
| 2007/0212321 A1 | 9/2007 | Braig et al. |
| 2008/0171658 A1 | 7/2008 | Dyllick-Brenzinger et al. |
| 2009/0053272 A1 | 2/2009 | Wagenblast |
| 2010/0015236 A1 | 1/2010 | Magdassi et al. |
| 2010/0179198 A1 | 7/2010 | Mertoglu et al. |
| 2010/0210465 A1 | 8/2010 | Li et al. |
| 2010/0227761 A1 | 9/2010 | Bruggemann et al. |
| 2011/0045975 A1 | 2/2011 | Ehr et al. |
| 2011/0081555 A1 | 4/2011 | Liu et al. |
| 2011/0189294 A1 | 8/2011 | Keiper et al. |
| 2012/0035054 A1 | 2/2012 | Ehr et al. |
| 2012/0184589 A1 | 7/2012 | Gewehr et al. |
| 2012/0214857 A1 | 8/2012 | Reinhard et al. |
| 2012/0264603 A1 | 10/2012 | Soane et al. |
| 2012/0329648 A1 | 12/2012 | Fowler et al. |
| 2013/0034650 A1 | 2/2013 | Li et al. |
| 2013/0274110 A1 | 10/2013 | Westbye et al. |
| 2013/0338223 A1 | 12/2013 | Reid et al. |
| 2014/0080702 A1 | 3/2014 | Schnabel et al. |
| 2014/0249031 A1 | 9/2014 | Mulqueen et al. |
| 2014/0294968 A1 | 10/2014 | Hofmann et al. |

FOREIGN PATENT DOCUMENTS

| | | |
|---|---|---|
| CN | 1491541 A | 4/2004 |
| EP | 0183999 A1 | 6/1986 |

OTHER PUBLICATIONS

Ng, W.K., et al., Rheological properties of methacrylic acid/ethyl acrylate co-polymer: comparison between an unmodified and hydrophobically modified system, Polymer, 42:249-259 (2001).

Written Opinion for PCT/IB2014/058816, 4 pages (May 28, 2014).

| Formulation | Type of Polymer in Nanoparticles | A.I. to Particle Weight Ratio | Target Abamectin Content | Measured Abamectin Content |
|---|---|---|---|---|
| Example 3 | S-MAA-NaAMPS | 5:1 | 10.0 | 10.0 |
| Example 4 | MAA-co-S | 1:1 | 2.0 | 1.8 |
| Example 5 | MAA-co-S | 1:1 | 4.1 | 3.5 |
| Example 6 | MAA-co-S | 1:2 | 2.1 | 1.8 |
| Example 7 | S-MAA-NaAMPS | 1:1 | 4.0 | 4.0 |
| Example 8 | S-MAA-NaAMPS | 1:2 | 4.0 | 3.6 |
| Example 9 | S-MAA-NaAMPS | 1:1 | 2.1 | 2.0 |

Figure 1

| Formulation | Parameter | Value after dilution to 40 ppm A.I. in CIPAC-D | Value after dilution to 200 ppm A.I. in CIPAC-D |
|---|---|---|---|
| Example 3 | Z-ave / PDI<br>Peak 1 (intensity)<br>Peak 2 (intensity) | 183.3 nm/0.165<br>216.4 nm (99.5%)<br>4983 nm (0.3%) | 184.6 nm / 0.155<br>210.7 nm (99.6%)<br>5069 nm (0.4%) |
| Example 4 | Z-ave / PDI<br>Peak 1 (intensity)<br>Peak 2 (intensity) | 172.5 nm / 0.169<br>206.5 nm (99.6%)<br>4563 nm / (0.4%) | N/A |
| Example 5 | Z-ave / PDI<br>Peak 1 (intensity)<br>Peak 2 (intensity) | 170.1 nm / 0.161<br>202.7 nm / (100%)<br>-- | N/A |
| Example 6 | Z-ave / PDI<br>Peak 1 (intensity)<br>Peak 2 (intensity) | 189.5 nm / 0.209<br>235.9 nm (99.8%)<br>4991 nm (0.2%) | N/A |
| Example 7 | Z-ave / PDI<br>Peak 1 (intensity)<br>Peak 2 (intensity) | 169.3 nm / 0.160<br>294.5 nm (99.5%)<br>5091 nm (0.3%) | N/A |
| Example 8 | Z-ave / PDI<br>Peak 1 (intensity)<br>Peak 2 (intensity) | 291.4 nm / 0.253<br>351.5 nm (98.8%)<br>4833 nm (1.2%) | N/A |
| Example 9 | Z-ave / PDI<br>Peak 1 (intensity)<br>Peak 2 (intensity) | 171.9 nm / 0.119<br>194.6 nm f(100%)<br>-- | N/A |

Figure 2

| Formulation from Example 3 | | DLS Measurements | | | HPLC (wt % a.i.) |
|---|---|---|---|---|---|
| | | Parameter Measured | Dilution to 200ppm in CIPAC-D | Dilution to 40ppm in CIPAC-D | |
| Immediately after Preparation | Fresh | Z-ave / PDI<br>Peak 1 (intensity)<br>Peak 2 (intensity) | 184.6 nm / 0.155<br>210.7 nm (99.6%)<br>5069 nm (0.4%) | 183.3 nm / 0.165<br>216.4 nm (99.5%)<br>4983 nm (0.3%) | 10.2 |
| | 24 hrs | Z-ave / PDI<br>Peak 1 (intensity)<br>Peak 2 (intensity) | 172.4 nm / 0.122<br>195.6 nm (100%)<br>-- | 172.4 nm / 0.124<br>191.3 nm (100%)<br>-- | 10.2 |
| After 8 Days | Fresh | Z-ave / PDI<br>Peak 1 (intensity)<br>Peak 2 (intensity) | 178.8 nm / 0.151<br>209.4 nm (99.8%)<br>4339 nm (0.2%) | 177.5 nm / 0.153<br>204.2 nm (99.6%)<br>4880 nm (0.4%) | Not Measured |
| After 27 Days | Fresh | Z-ave / PDI<br>Peak 1 (intensity)<br>Peak 2 (intensity) | Not Measured | 180.4 nm / 0.148<br>206.8 nm (99.8%)<br>5029 nm (0.2%) | 10.0 |

Figure 3

MECTIN AND MILBEMYCIN POLYELECTROLYTE NANOPARTICLE FORMULATIONS

REFERENCE TO RELATED APPLICATIONS

This application claims priority to U.S. Provisional Patent Application Ser. No. 61/760,902 filed Feb. 5, 2013, the entire contents of which is hereby incorporated by reference.

BACKGROUND

Mectin insecticides are used in a wide variety of crop protection applications including field crops, fruit trees, cotton and ornamentals, with the most common use being in citrus crops and pome fruits. Mectins are used typically to target pests such as mites (e.g., red mites), some members of the Lepidoptera family and some dipterous leafminers. Another common target for control with mectins is nematodes, generally in a seed treatment and in combination with another insecticide and/or fungicide. Exemplary mectins include abamectin, emamectin, ivermectin, doramectin, eprinomectin and selamectin, though several are primarily used in animal health. Mectins have a common chemical structural feature; they are macrocyclic lactones, generally including a base 16-membered ring. This structure is shared with two other groups of insecticides, milbemycins, described below, and spinosyns.

Closely related to mectin insecticides are milbemycin insecticides and spinosyn insecticides. Milbemycins are commonly used to control nematodes in tea crops and in silviculture, amongst other crop protection applications. Exemplary milbemycins include but are not limited to milbemectin, lepimectin, moxidectin, milbemectin oxime. Also related to mectins are spinosyn insecticides (e.g., spinosad and spinetoram) which are related to mectin and milbemycins by chemical structure and origin, but differ in their mode of action. Mectins and milbemycins act as chlorine channel activators but spinosyns are nicotinic acetylcholine receptor allosteric activators.

Mectins milbemycins are fermentation products of soil microorganisms of the *Streptomyces* genus. Eight different mectins can be isolated, and the eight different compounds form four pairs of homologs, though one member of the pair generally found in much higher abundance that the minor member of the pair. Exemplary ratios are generally greater than 4 to 1. Likewise, milbemycins are found in homolog pairs. Abamectin was the first candidate found to have insecticide properties and was the first introduced to the market. In addition to being an insecticide, abamectin has shown acaricide and nemacide properties when mites and nematodes are targeted. Emamectin, a derivative of abamectin was subsequently developed and marketed for control of Lepidoptera. Other mectins include ivermectin, eprinomectin, doramectin and selamectin, which are typically used in animal husbandry as antiparasitic drugs.

Mectins and milbemycins are very potent against mites, insects and nematodes, with lethal concentration ($LC_{90}$) values in the range of 0.1 to 0.01 ppm. The efficacy of the insecticides within each class and among these two classes can vary. Despite the lethality of these compounds, they do pose some drawbacks for users including rapid degradation, photolysis and low soil motility and thus rapid soil degradation by soil microorganisms. Some compounds are taken up by the treated plant, particularly within leaves, and demonstrate some residual activity against mites, however, macrocyclic lactones are not phloem and xylem mobile, and therefore do not show a true systemic effect.

SUMMARY OF THE INVENTION

The present disclosure provides formulations of mectin or milbemycin compounds including nanoparticles of polymer-associated mectin or milbemycin compounds with various formulating agents. The present disclosure also provides methods of producing and using these formulations.

In various embodiments, the present disclosure presents formulations including a nanoparticle including a polymer-associated mectin or milbemycin compound with an average diameter of between about 1 nm and about 500 nm; and the polymer is a polyelectrolyte and a dispersant or a wetting agent.

In some embodiments, the nanoparticle has a diameter of between about 1 nm and about 100 nm. In some embodiments, the nanoparticle has a diameter of between about 1 nm and about 20 nm. In some embodiments, the formulation includes a plurality of nanoparticles, wherein the nanoparticles are in an aggregate and the aggregate has a diameter of between about 10 nm and about 5000 nm. In some embodiments, the formulation includes a plurality of nanoparticles, wherein the nanoparticles are in an aggregate and the aggregate has a diameter of between about 100 nm and about 2500 nm. In some embodiments, the formulation includes a plurality of nanoparticles, wherein the nanoparticles are in an aggregate and the aggregate has a diameter of between about 100 nm and about 1000 nm. In some embodiments, the formulation includes a plurality of nanoparticles, wherein the nanoparticles are in an aggregate and the aggregate has a diameter of between about 100 nm and about 300 nm.

In some embodiments, the ratio of mectin and/or milbemycin compound to polymer within the nanoparticles is between about 10:1 and about 1:10. In some embodiments, the ratio of triazole compound to polymer within the nanoparticles is between about 5:1 and about 1:5. In some embodiments, the ratio of triazole compound to polymer within the nanoparticles is between about 2:1 and about 1:2. In some embodiments, the ratio of triazole compound to polymer within the nanoparticles is about 1:3. In some embodiments, the ratio of triazole compound to polymer within the nanoparticles is about 3:2. In some embodiments, the ratio of triazole compound to polymer within the nanoparticles is about 4:1. In some embodiments, the ratio of triazole compound to polymer within the nanoparticles is about 2:1. In some embodiments, the ratio of triazole compound to polymer within the nanoparticles is about 1:1. In some embodiments, the triazole compound is difenoconazole.

In some embodiments, the mectin or milbemycin compound is abamectin.

The formulation of any one of the preceding claims, wherein the polymer is selected from the group consisting of poly(methacrylic acid co-ethyl acrylate); poly(methacrylic acid-co-styrene); poly(methacrylic acid-co-styrene-co-sodium acrylamide-2-methylpropanesulfonate); poly(methacrylic acid-co-butylmethacrylate); poly[acrylic acid-co-polyethylene glycol)methyl ether methacrylate]; poly(n-butylmethacrylate-co-methacrylic acid) and poly(acrylic acid-co-styrene.

In some embodiments, the polymer is a homopolymer. In some embodiments, the polymer is a copolymer. In some embodiments, the polymer is a random copolymer.

In some embodiments, the dispersant and/or wetting agent is selected from the group consisting of lignosulfonates, organosilicones, methylated or ethylated seed oils, ethoxylates, sulfonates, sulfates and combinations thereof. In some embodiments, wherein the dispersant and/or wetting agent is sodium lignosulfonate. In some embodiments, wherein the dispersant and/or wetting agent is a tristyrylphenol ethoxylate.

In some embodiments, the wetting agent and the dispersant are the same compound. In some embodiments, the wetting agent and the dispersant are different compounds.

In some embodiments, the formulation excludes any wetting agent. In some embodiments, the formulation excludes excluding any dispersant.

In some embodiments, the wetting agent is less than about 30 weight % of the formulation. In some embodiments, the wetting agent is less than about 5 weight % of the formulation. In some embodiments, the dispersant is less than about 30 weight % of the formulation. In some embodiments, the dispersant is less than about 5 weight % of the formulation. In some embodiments, formulation is in the form of a high solids liquid suspension or a suspension concentrate.

In some embodiments, the formulation also includes between about 0.05 weight % and about 5 weight % of a thickener. In some embodiments, the thickener is less than about 1 weight % of the formulation. In some embodiments, the thickener is less than about 0.5 weight % of the formulation. In some embodiments, the thickener is less than about 0.1 weight % of the formulation. In some embodiments, the thickener is selected from the group consisting of guar gum; locust bean gum; xanthan gum; carrageenan; alginates; methyl cellulose; sodium carboxymethyl cellulose; hydroxyethyl cellulose; modified starches; polysaccharides and other modified polysaccharides; polyvinyl alcohol; glycerol alkyd, fumed silica and combinations thereof.

In some embodiments, the formulation also includes between about 0.01 weight % and about 0.2 weight % of a preservative. In some embodiments, the preservative is less than about 0.1 weight % of the formulation. In some embodiments, the preservative is less than about 0.05 weight % of the formulation. In some embodiments, the preservative is selected from the group consisting of tocopherol, ascorbyl palmitate, propyl gallate, butylated hydroxyanisole (BHA), butylated hydroxytoluene (BHT), propionic acid and its sodium salt; sorbic acid and its sodium or potassium salts; benzoic acid and its sodium salt; p-hydroxy benzoic acid sodium salt; methyl p-hydroxy benzoate; 1,2-benzisothiazalin-3-one, and combinations thereof.

In some embodiments, the formulation also includes between about 0.05 weight % and about 10 weight % of an anti-freezing agent. In some embodiments, the anti-freezing agent is less than about 5 weight % of the formulation. In some embodiments, the anti-freezing agent is less than about 1 weight % of the formulation. In some embodiments, the anti-freezing agent is selected from the group consisting of ethylene glycol; propylene glycol; urea and combinations thereof.

In some embodiments, the nanoparticles of polymer-associated mectin or milbemycin comprise less than about 80 weight % of the formulation. In some embodiments, the nanoparticles of polymer-associated mectin or milbemycin comprise between about 20 weight % and about 80 weight % of the formulation.

In some embodiments, the nanoparticles of polymer-associated mectin or milbemycin comprise about 20 weight % and about 50 weight % of the formulation. In some embodiments, the polymer-associated mectin or milbemycin compound is between about 5 weight % and about 40 weight % of the formulation. In some embodiments, the mectin or milbemycin compound is selected from the group consisting of abamectin, emamectin, milbemectin and combinations thereof.

In some embodiments, the formulation also includes an inert filler.

In some embodiments, the inert filler makes up less than about 90 weight % of the formulation. In some embodiments, the inert filler makes up less than about 40 weight % of the formulation. In some embodiments, the inert filler makes up less than about 5 weight % of the formulation. In some embodiments, the inert filler is selected from the group consisting of saccharides, celluloses, starches, carbohydrates, vegetable oils, protein inert fillers, polymers and combinations thereof.

In some embodiments, the formulation also includes between about 1 weight % and about 20 weight % of a disintegrant. In some embodiments, the formulation also includes between about 0.05 weight % and about 3 weight % of an anti-caking agent. In some embodiments, the anti-caking agent is less than about 1 weight % of the formulation.

In some embodiments, the formulation also includes between about 0.05 weight % and about 5 weight % of an anti-foaming agent. In some embodiments, the anti-foaming agent is less than about 1 weight % of the formulation.

In some embodiments, the formulation also includes comprising between about 1 weight % and about 20 weight % of a non-ionic surfactant. In some embodiments, the non-ionic surfactant is less than about 1 weight % of the formulation.

In some embodiments, the formulation is diluted so that the concentration of the polymer-associated mectin or milbemycin compound is between about 0.1 to about 1000 ppm. In some embodiments, the formulation is diluted so that the concentration of the polymer-associated mectin or milbemycin compound is between about 10 to about 500 ppm.

In some embodiments, the formulation also includes contains a fungicide and/or a pesticide.

In various aspects, the present disclosure describes a method of using the formulation of any one of the preceding claims including the steps of, applying the formulation to a plant.

In some embodiments, the formulation is applied to one part of a plant and the mectin or milbemycin translocates to an unapplied part of the plant.

In some embodiments, the unapplied part of the plant comprises new plant growth since the application.

In various aspects, the present disclosure describes a method of inoculating a plant with a mectin or milbemycin against a pest by applying any of the formulations described herein, to the plant.

In various aspects, the present disclosure describes a method of treating a pest infestation of a plant with a mectin or milbemycin by applying any of the formulations described herein to the plant.

In various aspects, the present disclosure describes a method of increasing a plant's pest resistance by applying any of the formulations described herein to the plant.

In some embodiments, the plant to which the formulation is applied is selected from the classes fabaceaae, brassicaceae, rosaceae, solanaceae, convolvulaceae, poaceae, amaranthaceae, laminaceae and apiaceae.

In some embodiments, the plant is selected from oil crops, cereals, pasture, turf, ornamentals, fruit, legume vegetables, bulb vegetables, cole crops, tobacco, soybeans, cotton, sweet corn, field corn, potatoes and greenhouse crops.

BRIEF DESCRIPTION OF THE DRAWINGS

FIG. 1 is a table listing the compositions of the formulations prepared in Examples 3-9.

FIG. 2 is a table listing the particle size at two dilutions and the polydispersity index of the various formulations described in Examples 3-9.

FIG. 3 is a table listing particle size and active ingredient concentration of the formulation prepared in Example 3 after varying storage periods. The formulation was prepared according to the example, and diluted in CIPAC D water to 200 ppm or 40 ppm either immediately after formulation, after 8 days or after 27 days of storage. For the sample diluted immediately after formulation, particle size and active ingredient concentration were measure immediately after dilution, and again 24 hours after dilution.

DEFINITIONS

As used herein, the term "inoculation" refers to a method used to administer or apply a formulation of the present invention to a target area of a plant or pest. The inoculation method can be, but is not limited to, aerosol spray, pressure spray, direct watering, and dipping. Target areas of a plant could include, but are not limited to, the leaves, roots, stems, buds, flowers, fruit, and seed. Target areas of a pest (e.g., insect) could include, but are not limited to, the head, eyes, maxilla, mandible, antennae, thorax, leg, wings, and abdomen. Inoculation can include a method wherein a plant is treated in one area (e.g., the root zone or foliage) and another area of the plant becomes protected (e.g., foliage when applied in the root zone or new growth when applied to foliage).

As used herein, the term "wettable granule" also referred to herein as "WG", "water dispersible granule", and "dispersible granule" refers to a solid granular formulation that is prepared by a granulation process and that contains nanoparticles of polymer-associated active ingredient, or aggregates of the same, a wetting agent and/or a dispersant, and optionally an inert filler. Wettable granules can be stored as a formulation, and can be provided to the market and/or end user without further processing. In some embodiments, they can be placed in a water-soluble bag for ease of use by the end user. In practical application, wettable granules are prepared for application by the end user. The wettable granules are mixed with water in the end user's spray tank to the proper dilution for the particular application. Dilution can vary by crop, pest, time of year, geography, local regulations, and intensity of infestation among other factors. Once properly diluted, the solution can be applied by spraying.

As used herein, the term "wettable powder" also referred to herein as "WP", "water dispersible powder" and "dispersible powder", refers to a solid powdered formulation that contains nanoparticles of polymer-associated active ingredient, or aggregates of the same, and optionally one or more of a dispersant, a wetting agent, and an inert filler. Wettable powders can be stored as a formulation, and can be provided to the market and/or end user without further processing. In some embodiments, they can be placed in a water-soluble bag for ease of use by the end user. In practical application, a wettable powder is prepared for application by the end user. The wettable powder is mixed with water in the end user's spray tank to the proper dilution for the particular application. Dilution can vary by crop, pest, time of year, geography, local regulations, and intensity of infestation among other factors. Once properly diluted, the solution can be applied by spraying.

As used herein, the term "high solids liquid suspension" also referred to herein as "HSLS" refers to a liquid formulation that contains nanoparticles of polymer nanoparticles associated with active ingredient, or aggregates of the same, a wetting agent and/or a dispersant, an anti-freezing agent, optionally an anti-settling agent or thickener, optionally a preservative, and water. High solids liquid suspensions can be stored as a formulation, and can be provided to the market and/or end user without further processing. In practical application, high solids liquid suspensions are prepared for application by the end user. The high solids liquid suspensions are mixed with water in the end user's spray tank to the proper dilution for the particular application. Dilution can vary by crop, pest, time of year, geography, local regulations, intensity of infestation among other factors. Once properly diluted, the solution can be applied by spraying.

DESCRIPTION OF VARIOUS EMBODIMENTS OF THE INVENTION

As described above mectin and milbemycins insecticides are used in a wide variety of crop protection applications. Though they are typically used to target pests such as mites (e.g., red mites); they can be used to control nematodes, generally in a seed treatment and in combination with another insecticide and/or fungicide. Exemplary mectins include abamectin, emamectin, ivermectin, doramectin, eprinomectin and selamectin, though several are primarily used in animal health.

Mectins and milbemycins, whether naturally occurring or synthetic, interact with ligand-gated chloride channels within nerve cells of the target organism. Specifically, these compounds function in glutamate-gated chloride channels and γ-aminobutyric acid (GABA) receptors. By binding the neurotransmitter (e.g., glutamate or GABA) the channel becomes permeable to chloride ions. This increase in permeability allows more chloride ions into nerves which in turn disrupts the organism's nervous system function. The organism is typically paralyzed.

Solubility

Mectins and milbemycins as a class are typically poorly soluble in water, generally with solubilities in the parts per million range or lower. Mectin solubilities are improved in organic solvents, as indicated below, however solvents are either not application to agricultural usage or strongly disfavored. See Table 1 below for a list of typical mectins and milbemycins, their solubilities in water as well as other organic solvents, and octanol-water partition coefficients. (Data via the Pesticide Properties Database)

TABLE 1

Solubility of exemplary mectins and milbemycins in common solvents, octanol-water partition coefficients and melting points

| Insecticide | Solubility (all at 20° C.) | Octanol-Water Coefficient |
|---|---|---|
| abamectin | Water: 1.21 mg/L<br>Acetone: 72,000 mg/L<br>Ethyl Acetate: 160,000 mg/L | Log P: 4.4 |
| emamectin | Water: 24 mg/L<br>Methanol: 2700 g/L | Log P: 5.0 |
| milbemycin | Water 3.6 mg/L<br>Methanol: 251,000 mg/L<br>n-heptane: 5,060 mg/L | Log P: 6.8 |

Improvements in the solubility of mectins and milbemycins are desirable in order to improve formulation processes, simplify formulations, reduce the environmental consequences in insecticide application and improve insecticide efficacy.

Photolytic Stability Mectins and milbemycins degrade upon exposure to sunlight and demonstrate a range of half-lives as listed in Table 2

TABLE 2

Photolytic Stability of exemplary mectins and milbemycins

| Insecticide | Aqueous Photolysis |
| --- | --- |
| abamectin | DT50: 1.5 d at pH 7 |
| emamectin | DT50: 32 d at pH 7 |
| milbemycin | DT50: 3 d at pH 5 (aqueous hydrolysis DT50 = 2.6 d) |

Due to the tendency of mectins and milbemycins to degrade upon exposure to sunlight, many crop protection formulations of mectins and milbemycins employ a UV blocker such as zinc, tin or iron oxides as well as organic UV blockers (e.g., 1,2-dihydroxybenzophenone). The use of UV-blockers in formulation can present additional complications in formulating, application and use. For example, the UV-blocker is an additional component that needs to be soluble or at least dispersible in the media or matrix of the product. It is therefore desirable to produce formulations that do not require a UV-blocker.

Formulations—Generally

Several mectin and milbemycin formulations are currently commercially available, the bulk of which are used in agricultural applications. The aforementioned limitations of mectins and milbemycins, and their formulations, when used as insecticides manifest themselves in (a) how they are currently applied to plants and (b) how they are formulated by manufacturers. As an example, because mectin and milbemycin compounds are susceptible to degradation (either from photolysis or exposure of field conditions) end users (e.g., farmers or golf course maintenance managers) need to apply the insecticide more often than if they were longer lasting. As another example, because mectins and milbemycins lack true systemic activity (which would help protect new growth of crops), end users need to continually re-apply the insecticides in order to protect crops from infection. These limitations are compounded by increasing pressure on end users who are faced with increasing regulatory and consumer pressure to use fewer pesticides and/or fungicides and in lower quantities.

In order to address these limitations, a variety of complicated formulation techniques and formulation agents have been developed to counter to the UV instability, water insolubility, non-systemic nature, and other limitations of mectins.

In order for a mectin or a milbemycin to be efficiently applied to a plant, the product needs to be dispersible in water. One common formulation technique to do this is to produce emulsifiable concentrate (EC), though suspension concentrates (SC), described below, can be formulated with mectins and milbemycins. An EC is a formulation where the active ingredient is dissolved in a suitable solvent in the presence of surfactants. When the EC is dispersed into the spray tank and agitated, the surfactants emulsify the solvent into water, and the active ingredient is delivered in the solvent phase to the plant. Other common formulation techniques used for some crop protection active ingredients, particularly mectins and milbemycins include microencapsulations (CS) and emulsions (EW or OW). Solid formulation techniques that are currently used include water-dispersible granules (WG) or powders (WP), where the active ingredient is absorbed to a dispersible carrier that is provided dry to the farmer. When mixed into the spray tank, the carrier disperses into the water, carrying the active ingredient with it. Particle sizes for these carriers can be anywhere in the range of 1-10 microns (Alan Knowles, *Agrow Reports: New Developments in Crop Protection Product Formulation*. London: Agrow Reports May 2005).

A SC is a high-solids concentrate in water. The active ingredient is milled into particles that are 1-10 microns (Alan Knowles, Agrow Reports: New Developments in Crop Protection Product Formulation. London: Agrow Reports May 2005). These solid particles are then dispersed into water at high concentration using surfactants. After adding the SC into the spray tank, the surfactant-stabilized particles disperse into water and are applied (still as solid particles) to the leaf surface. Other common formulation techniques used for some crop protection active ingredients include microencapsulations (CS) and emulsions (EW or OW). Solid formulation techniques that are currently used include water-dispersible granules (WG) or powders (WP), where the active ingredient is absorbed to a dispersible carrier that is provided dry to the farmer. When mixed into the spray tank, the carrier disperses into the water, carrying the active ingredient with it. Particle sizes for these carriers can be anywhere in the range of 1-10 microns (Alan Knowles, Agrow Reports: New Developments in Crop Protection Product Formulation. London: Agrow Reports May 2005).

As an alternative to these approaches, we have developed new classes mectin and milbemycin formulations. As demonstrated in the Examples and as discussed below, in some embodiments these new mectin and milbemycin formulations are more dispersible in water and have enhanced stability (i.e., longer lasting) and do not use organic solvents. Further, the new formulations are also compatible with other agricultural products (surfactants, leaf wetters, fertilizers, etc.), and are stable in non-ideal solution conditions such high salt, extreme pH, hard water, elevated temperatures, etc. These enhancements/improvements in the formulation can also help address the resistance of some pests by being (1) compatible with a second pesticide (e.g., another insecticide, a fungicide, etc. . . . ), either tank-mixed or pre-mixed in the original formulation and (2) requiring less pesticide in each application as well as improved efficacy and reduced application rates. In general, these new mectin or milbemycin formulations comprise nanoparticles (optionally in aggregate form) of polymer-associated mectins or milbemycins along with various formulating agents.

Additionally, because the instant formulations are based around nanoparticles of polymer-associated active ingredients, they are stable to relatively high salt conditions. Stability in high salt conditions is required especially when the formulation is to be mixed with other secondary agricultural products such as a concentrated fertilizer mix, exposed to high salt conditions (e.g., used in or with hard waters) mixed with other formulations (other pesticides, fungicides, and herbicides) or mixed with other tank-mix adjuvants. The ability to mix our formulations with other products can be beneficial to the end user because simultaneous agricultural products can be applied in a single application.

Soil Mobility

Most mectins and milbemycins are substantially immobile in soil and are unlikely to move via leaching. Without wishing to be bound by any theory, the low soil mobility is thought to be primarily due to the mectins and milbemycins non-polar nature and lack of water solubility. When mectins and milbemycins are dispersed in water they therefore have a tendency to associate with natural organic matter found in soils and, once bound to the top soil's organic matter, exhibit low mobility within the surrounding soil matrix. This lack of soil mobility limits the pests that can be targeted with mectins and milbemycins, especially some soil-borne pests (e.g. nematodes) that may reside beneath the top soil area. It would therefore be desirable to provide mectins and milbemycins formulations that have moderate soil mobility to allow the active to penetrate in the soil matrix.

Formulations—Components

In various aspects, the present disclosure provides formulations that comprise nanoparticles (optionally in aggregate form) of polymer-associated active ingredient along with various formulating agents.

Active Ingredient

As used herein, the term "active ingredient" ("ai", "AI", "a.i.", "A.I.") refers to mectin and/or milbemycin compounds (i.e., abamectin). Structurally, the basic common feature in this family is the presence of 16-membered macrocyclic lactone. The structure of abamectin (form $B_{1a}$) is below:

Non limiting examples of mectins and milbemycins abamectin, doramectin, emamectin, eprinomectin, ivermectin, selamectin, lepimectin, milbemectin, milbemycin oxime, moxidectin. Spinosyn insecticides are also active ingredients that can be used in the formulations disclosed herein. Exemplary spinosyn insecticides include, but are not limited to, spinosad and spinetoram.

Nanoparticles of Polymer-Associated Active Ingredient

As used herein, the terms "nanoparticles of polymer-associated active ingredient", "nanoparticles of polymer-associated mectin or milbemycin compound" or "active ingredient associated with polymer nanoparticles" refer to nanoparticles comprising one or more collapsed polymers that are associated with the active ingredient. In some embodiments the collapsed polymers are cross-linked. As discussed below, in some embodiments, our formulations may include aggregates of nanoparticles. Exemplary polymers and methods of preparing nanoparticles of polymer-associated active ingredient are described more fully below.

In some embodiments, the active ingredient is associated with preformed polymer nanoparticles. The associating step may involve dispersing the polymer nanoparticles in a first solvent and then dispersing the active ingredient in a second solvent that is miscible or partially miscible with the first solvent, mixing the two dispersions and then either removing the second or first solvent from the final mixture. In some embodiments, all the solvent is removed by vacuum evaporation, freeze drying or spray drying. The associating step may also involve dispersing both the preformed polymer nanoparticles and active ingredients in a common solvent and removing all or a portion of the common solvent from the final mixture.

In some embodiments, the associating step may involve milling the active ingredient in the presence of pre-formed polymer nanoparticles. It is surprising that if the active ingredient alone is milled under these conditions; the resulting particle size is significantly larger than if it is milled in the presence of pre-formed polymer nanoparticles. In general, size reduction processes such as milling do not enable the production of particle sizes that are produced via milling in the presence of nanoparticles of the current disclosure. Without wishing to be bound by any theory, it is thought that interaction between the active ingredient and the nanoparticles during the milling process facilitates the production of smaller particles than would be formed via milling in the absence of the nanoparticles.

Non-limiting examples of milling methods that may be used for the association step can be found in U.S. Pat. No. 6,604,698 and include ball milling, bead milling, jet milling, media milling, and homogenization, as well as other milling methods known to those of skill in the art. Non-limiting examples of mills that can be for the association step include attritor mills, ball mills, colloid mills, high pressure homogenizers, horizontal mills, jet mills, swinging mills, and vibratory mills. In some embodiments, the associating step may involve milling the active ingredient in the presence of pre-formed polymer nanoparticles and an aqueous phase. In some embodiments, the associating step may involve wet or dry milling of the active ingredient in the presence of pre-formed nanoparticles. In some embodiments, the association step may involve milling the active ingredient and pre-formed polymer nanoparticles in the presence of one or more formulating agents.

In general and without limitation, the active ingredient may be associated with regions of the polymer nanoparticle that elicit a chemical or physical interaction with the active ingredient. Chemical interactions can include hydrophobic interactions, affinity pair interactions, H-bonding, and van der Waals forces. Physical interactions can include entanglement in polymer chains and/or inclusion within the polymer nanoparticle structure. In some embodiments, the active ingredient can be associated in the interior of the polymer nanoparticle, on the surface of the polymer nanoparticle, or both the surface and the interior of the polymer nanoparticle. Furthermore, the type of association interactions between the active ingredient and the polymer nanoparticle can be probed using spectroscopic techniques such as NMR, IR, UV-vis, and emission spectroscopies. For example, in cases where the mectin or milbemycin active ingredient is normally crystalline when not associated with the polymer nanoparticles, the nanoparticles of polymer-associated mectin or milbemycin compounds typically do not show the endothermic melting peak or show a reduced endothermic melting peak of the pure crystalline active ingredient as seen in differential thermal analysis (DTA) or differential scanning calorimetry (DSC) measurements.

Nanoparticles of polymer-associated active ingredients can be prepared with a range of average diameters, e.g., between about 1 nm and about 500 nm. The size of the nanoparticles can be adjusted in part by varying the size and number of polymers that are included in the nanoparticles. In some embodiments, the average diameter ranges from about 1 nm to about 10 nm, from about 1 nm to about 20 nm, from about 1 nm to about 30 nm, from about 1 nm to about 50 nm, from about 10 nm to about 50 nm, from about 10 nm to about 100 nm, from about 20 nm to about 100 nm, from about 20 nm to about 100 nm, from about 50 nm to about 200 nm, from about 50 nm to about 250 nm, from about 50 nm to about 300 nm, from about 100 nm to about 250 nm, from about 100 nm to about 300 nm, from about 200 nm to about 300 nm, from about 200 nm to about 500 nm, from about 250 nm to about 500 nm, and from about 300 nm to about 500 nm. These and other average diameters described herein are based on volume average particle sizes that were measured in solution by dynamic light scattering on a Malvern Zetasizer ZS in CIPAC D water, 0.1M NaCl, or in deionized water at 200 ppm active concentration. Various forms of microscopies can also be used to visualize the sizes of the nanoparticles such as atomic force microscopy (AFM), transmission electron microscopy (TEM), scanning electron microscopy (SEM) and optical microscopy.

In some embodiments, the aggregates of nanoparticles of polymer-associated active ingredients have an average particle size between about 10 nm and about 5,000 nm when dispersed in water under suitable conditions. In some embodiments, the aggregates have an average particle size between about 10 nm and about 1,000 nm. In some embodiments, the aggregates have an average particle size between about 10 nm and about 500 nm. In some embodiments, the aggregates have an average particle size between about 10 nm and about 300 nm. In some embodiments, the aggregates have an average particle size between about 10 nm and about 200 nm. In some embodiments, the aggregates have an average particle size between about 50 nm and about 5,000 nm. In some embodiments, the aggregates have an average particle size between about 50 nm and about 1,000 nm. In some embodiments, the aggregates have an average particle size between about 50 nm and about 500 nm. In some embodiments, the aggregates have an average particle size between about 50 nm and about 300 nm. In some embodiments, the aggregates have an average particle size between about 50 nm and about 200 nm. In some embodiments, the aggregates have an average particle size between about 100 nm and about 5,000 nm. In some embodiments, the aggregates have an average particle size between about 100 nm and about 1,000 nm. In some embodiments, the aggregates have an average particle size between about 100 nm and about 500 nm. In some embodiments, the aggregates have an average particle size between about 100 nm and about 300 nm. In some embodiments, the aggregates have an average particle size between about 100 nm and about 200 nm. In some embodiments, the aggregates have an average particle size between about 500 nm and about 5000 nm. In some embodiments, the aggregates have an average particle size between about 500 nm and about 1000 nm. In some embodiments, the aggregates have an average particle size between about 1000 nm and about 5000 nm. Particle size can be measured by the techniques described above.

As described in detail in the examples, in some embodiments, pre-formed polymer nanoparticles that have been associated with active ingredient to generate nanoparticles or aggregates of nanoparticles of polymer-associated active ingredients (associated nanoparticles) can be recovered after extraction of the active ingredient. In some embodiments, the active ingredient can be extracted from nanoparticles or aggregates of nanoparticles of polymer-associated active ingredient by dispersing the associated nanoparticles in a solvent that dissolves the active ingredient but that is known to disperse the un-associated, preformed nanoparticles poorly or not at all. In some embodiments, after extraction and separation, the insoluble nanoparticles that are recovered have a size that is smaller than the nanoparticles or aggregates of nanoparticles of polymer-associated active ingredients as measured by DLS. In some embodiments, after extraction and separation, the insoluble nanoparticles that are recovered have a size that is similar or substantially the same as the size of original pre-formed polymer nanoparticles (prior to association) as measured by DLS. In some embodiments, the nanoparticles are prepared from poly(methacrylic acid-co-ethyl acrylate). In some embodiments, the active ingredient is abamectin. In some embodiments, the extraction solvent is acetonitrile.

It should be understood that the association step to generate nanoparticles of polymer associated active ingredient need not necessarily lead to association of the entire fraction the active ingredient in the sample with pre-formed polymer nanoparticles (not all molecules of the active ingredient in the sample must be associated with polymer nanoparticles after the association step). Likewise, the association step need not necessarily lead to the association of the entire fraction of the pre-formed nanoparticles in the sample with active ingredient (not all nanoparticle molecules in the sample must be associated with the active ingredient after the association step).

Similarly, in formulations comprising nanoparticles of polymer-associated active, the entire fraction of active ingredient in the formulation need not be associated with pre-formed polymer nanoparticles (not all molecules of the active ingredient in the sample must be associated with polymer nanoparticles in the formulation). Likewise, in formulations comprising nanoparticles of polymer-associated active ingredient, the entire fraction of pre-formed polymer nanoparticles in the formulation need not be associated with active ingredient (not all of nanoparticle molecules in the sample must be associated with the active ingredient in the formulation).

In some embodiments, the nanoparticles are prepared using a polymer that is a polyelectrolyte. Polyelectrolytes are polymers that contain monomer units of ionized or ionizable functional groups. They can be linear, branched, hyper-branched or dendrimeric, and they can be synthetic or naturally occurring. Ionizable functional groups are functional groups that can be rendered charged by adjusting solution conditions, while ionized functional group refers to chemical functional groups that are charged regardless of solution conditions. The ionized or ionizable functional group can be cationic or anionic, and can be continuous along the entire polymer chain (e.g., in a homopolymer), or can have different functional groups dispersed along the polymer chain, as in the case of a co-polymer (e.g., a random co-polymer). In some embodiments, the polymer can be made up of monomer units that contain functional groups that are either anionic, cationic, both anionic and cationic, and can also include other monomer units that impart a specific desirable property to the polymer.

In some embodiments, the polyelectrolyte is a homopolymer. Non limiting examples of homopolymer polyelectrolytes include: poly(acrylic acid), poly(methacrylic acid), polystyrene sulfonate), poly(ethyleneimine), chitosan, poly (dimethylammonium chloride), poly(allylamine hydrochloride), and carboxymethyl cellulose.

In some embodiments, the polyelectrolyte is a co-polymer. Non limiting examples of co-polymer polyelectrolytes include: poly(methacrylic acid-co-ethyl acrylate); poly (methacrylic acid-co-styrene); poly(methacrylic acid-co-butylmethacrylate); poly[acrylic acid-co-polyethylene glycol) methyl ether methacrylate].

In some embodiments, the polyelectrolyte can be made from one or more monomer units to form homopolymers, copolymers or graft copolymers of: ethylene; ethylene glycol; ethylene oxide; carboxylic acids including acrylic acid, methacrylic acid, itaconic acid, and maleic acid; polyoxyethylenes or polyethyleneoxide; and unsaturated ethylenic mono or dicarboxylic acids; lactic acids; amino acids; amines including dimethylammonium chloride, allylamine hydrochloride; methacrylic acid; ethyleneimine; acrylates including methyl acrylate, ethyl acrylate, propyl acrylate, n-butyl acrylate ("BA"), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, and z; vinylnapthalene, vinylnaphthalene sulfonate, vinylpyrrolidone, vinyl alcohol; aminoalkyls including aminoalkylacrylates, aminoalkylsmethacrylates, and aminoalkyl(meth)acrylamides; styrenes including styrene sulfonate; d-glucosamine; glucaronic acid-N-acetylglucosamine; N-isopropylacrylamide; vinyl amine. In some embodiments, the polyelectrolyte polymer can include groups derived from polysaccharides such as dextran, gums, cellulose, or carboxymethyl cellulose.

In some embodiments, the polyelectrolyte comprises poly(methacrylic acid-co-ethyl acrylate) polymer. In some embodiments, the mass ratio of methacrylic acid to ethyl acrylate in the poly(methacrylic acid-co-ethyl acrylate) polymer is between about 50:50 and about 95:5. In some embodiments, the mass ratio of methacrylic acid to ethyl acrylate in the poly(methacrylic acid-co-ethyl acrylate) polymer is between about 70:30 and about 95:5. In some embodiments, the mass ratio of methacrylic acid to ethyl acrylate in the poly(methacrylic acid-co-ethyl acrylate) polymer is between about 80:20 and about 95:5. In some embodiments, the mass ratio of methacrylic acid to ethyl acrylate in the poly(methacrylic acid-co-ethyl acrylate) polymer is between about 85:15 and about 95:5. In some embodiments, the mass ratio of methacrylic acid to ethyl acrylate in the poly(methacrylic acid-co-ethyl acrylate) polymer is between about 60:40 and about 80:20.

In some embodiments, the polyelectrolyte comprises poly(methacrylic acid-co-styrene) polymer. In some embodiments, the mass ratio of methacrylic acid to styrene in the poly(methacrylic acid-co-styrene) polymer is between about 50:50 and about 95:5. In some embodiments, the mass ratio of methacrylic acid to styrene in the poly(methacrylic acid-co-styrene) polymer is between about 70:30 and about 95:5. In some embodiments, the mass ratio of methacrylic acid to styrene in the poly(methacrylic acid-co-styrene) polymer is between about 80:20 and about 95:5. In some embodiments, the mass ratio of methacrylic acid to styrene in the poly(methacrylic acid-co-styrene) polymer is between about 85:15 and about 95:5. In some embodiments, the mass ratio of methacrylic acid to styrene in the poly(methacrylic acid-co-styrene) polymer is between about 60:40 and about 80:20.

In some embodiments, the mass ratio of methacrylic acid to butyl methacrylate in the poly(methacrylic acid-co-butylmethacrylate) polymer is between about 50:50 and about 95:5. In some embodiments, the mass ratio of methacrylic acid to butyl methacrylate in the poly(methacrylic acid-co-butylmethacrylate) polymer is between about 70:30 and about 95:5. In some embodiments, the mass ratio of methacrylic acid to butyl methacrylate in the poly(methacrylic acid-co-butylmethacrylate) polymer is between about 80:20 and about 95:5. In some embodiments, the mass ratio of methacrylic acid to butyl methacrylate in the poly(methacrylic acid-co-butylmethacrylate) polymer is between about 85:15 and about 95:5. In some embodiments, the mass ratio of methacrylic acid to butyl methacrylate in the poly(methacrylic acid-co-butylmethacrylate) polymer is between about 60:40 and about 80:20.

In some embodiments, the homo or co-polymer is water soluble at pH 7. In some embodiments, the polymer has solubility in water above about 1 weight %. In some embodiments, the polymer has solubility in water above about 2 weight %. In some embodiments, the polymer has solubility in water above about 3 weight %. In some embodiments, the polymer has solubility in water above about 4 weight %. In some embodiments, the polymer has solubility in water above about 5 weight %. In some embodiments, the polymer has solubility in water above about 10 weight %. In some embodiments, the polymer has solubility in water above about 20 weight %. In some embodiments, the polymer has solubility in water above about 30 weight %. In some embodiments, the polymer has solubility in water between about 1 and about 30 weight %. In some embodiments, the polymer has solubility in water between about 1 and about 10 weight %. In some embodiments, the polymer has solubility in water between about 5 and about 10 weight %. In some embodiments, the polymer has solubility in water between about 10 and about 30 weight %. In some embodiments the solubility of the polymer in water can also be adjusted by adjusting pH or other solution conditions in water.

In some embodiments, the polyelectrolyte polymer has a weight average ($M_w$) molecular weight between about 5,000 and about 4,000,000 Daltons. In some embodiments, the polyelectrolyte polymer has a weight average molecular weight between about 100,000 and about 2,000,000 Daltons. In some embodiments, the polyelectrolyte polymer has a weight average molecular weight between about 100,000 and about 1,000,000 Daltons. In some embodiments, the polyelectrolyte polymer has a weight average molecular weight between about 100,000 and about 750,000 Daltons. In some embodiments, the polyelectrolyte polymer has a weight average molecular weight between about 100,000 and about 500,000 Daltons. In some embodiments, the polyelectrolyte polymer has a weight average molecular weight between about 100,000 and about 200,000 Daltons. In some embodiments, the polyelectrolyte polymer has a weight average molecular weight between about 200,000 and about 2,000,000 Daltons. In some embodiments, the polyelectrolyte polymer has a weight average molecular weight between about 200,000 and about 1,000,000 Daltons. In some embodiments, the polyelectrolyte polymer has a weight average molecular weight between about 200,000 and about 500,000 Daltons. In some embodiments, the polyelectrolyte polymer has a weight average molecular weight between about 300,000 and about 2,000,000 Daltons. In some embodiments, the polyelectrolyte polymer has a weight average molecular weight between about 300,000 and about 1,000,000 Daltons. In some embodiments, the polyelectrolyte polymer has a weight average molecular weight between about 300,000 and about 500,000 Daltons. In some embodiments, the polyelectrolyte polymer has a weight average molecular weight between about 5,000 and about 250,000 Daltons. In some embodiments, the polyelectrolyte polymer has a weight average molecular weight between about 5,000 and about 50,000 Daltons. In some embodiments, the polyelectrolyte polymer has a weight average molecular weight between about 5,000 and about 100,000 Daltons. In some embodiments, the polyelectrolyte polymer has a weight average molecular weight between about 5,000 and about 250,000 Daltons. In some embodiments, the polyelectrolyte polymer has a weight average molecular weight between about 50,000 and about 250,000 Daltons.

In some embodiments, the apparent molecular weight of the polyelectrolyte polymer (e.g., the molecular weight determined via certain analytical measurements such as size exclusion chromatography or DLS) is lower than the actual molecular weight of a polymer due to crosslinking within the polymer. In some embodiments, a crosslinked polyelectrolyte polymer of the present disclosure might have a higher actual molecular weight than the experimentally determined apparent molecular weight. In some embodiments, a crosslinked polyelectrolyte polymer of the present disclosure might be a high molecular weight polymer despite having a low apparent molecular weight.

Nanoparticles of polymer-associated active ingredients and/or aggregates of these nanoparticles can be part of a formulation in different amounts. The final amount will depend on many factors including the type of formulation (e.g., liquid or solid, granule or powder, concentrated or not, etc.). In some instances the nanoparticles (including both the polymer and active ingredient components) make up between about 1 and about 98 weight % of the total formulation. In some embodiments, the nanoparticles make up between about 1 and about 90 weight % of the total formulation. In some embodiments, the nanoparticles make up between about 1 and about 75 weight % of the total formulation. In some embodiments, the nanoparticles make up between about 1 and about 50 weight % of the total formulation. In some embodiments, the nanoparticles make up between about 1 and about 30 weight % of the total formulation. In some embodiments, the nanoparticles make up between about 1 and about 25 weight % of the total formulation. In some embodiments, the nanoparticles make up between about 1 and about 10 weight % of the total formulation. In some embodiments, the nanoparticles make up between about 5 and about 15 weight % of the total formulation. In some embodiments, the nanoparticles make up between about 5 and about 25 weight % of the total formulation. In some embodiments, the nanoparticles make up between about 10 and about 25 weight % of the total formulation. In some embodiments, the nanoparticles make up between about 10 and about 30 weight % of the total formulation. In some embodiments, the nanoparticles make up between about 10 and about 50 weight % of the total formulation. In some embodiments, the nanoparticles make up between about 10 and about 75 weight % of the total formulation. In some embodiments, the nanoparticles make up between about 10 and about 90 weight % of the total formulation. In some embodiments, the nanoparticles make up between about 10 and about 98 weight % of the total formulation. In some embodiments, the nanoparticles make up between about 25 and about 50 weight % of the total formulation. In some embodiments, the nanoparticles make up between about 25 and about 75 weight % of the total formulation. In some embodiments, the nanoparticles make up between about 25 and about 90 weight % of the total formulation. In some embodiments, the nanoparticles make up between about 30 and about 98 weight % of the total formulation. In some embodiments, the nanoparticles make up between about 50 and about 90 weight % of the total formulation. In some embodiments, the nanoparticles make up between about 50 and about 98 weight % of the total formulation. In some embodiments, the nanoparticles make up between about 75 and about 90 weight % of the total formulation. In some embodiments, the nanoparticles make up between about 75 and about 98 weight % of the total formulation.

In some embodiments, the nanoparticles of polymer-associated active ingredients are prepared according to a method disclosed in United States Patent Application Publication No. 20100210465, the entire contents of which are incorporated herein by reference. In some embodiments, polymer nanoparticles without active ingredients are made by collapse of a polyelectrolyte with a collapsing agent and then rendering the collapsed conformation permanent by intra-particle cross-linking. The active ingredient is then associated with this pre-formed polymer nanoparticle. In some embodiments, the formulation contains the same amount (by weight) of active ingredient and polymer nanoparticle, while in other embodiments the ratio of active ingredient to polymer nanoparticle (by weight) can be between about 1:10 and about 10:1, between about 1:10 and about 1:5, between about 1:5 and about 1:4, between about 1:4 and about 1:3, between about 1:3 and about 1:2, between about 1:2 and about 1:1, between about 1:5 and about 1:1, between about 5:1 and about 1:1, between about 2:1 and about 1:1, between about 3:1 and about 2:1, between about 4:1 and about 3:1, between about 5:1 and about 4:1, between about 10:1 and about 5:1, between about 1:3 and about 3:1, between about 5:1 and about 1:1, between about 1:5 and about 5:1, or between about 1:2 and about 2:1.

As noted above, in some embodiments, the associating step may involve dispersing the polymer nanoparticles in a first solvent, dispersing the active ingredient in a second solvent that is miscible or partially miscible with the first solvent, mixing the two dispersions and then either removing the second or first solvent from the final mixture.

Alternatively, in some embodiments, the associating step may involve dispersing both the pre-formed polymer nanoparticles and active ingredient in a common solvent and removing all or a portion of the common solvent from the final mixture. The final form of the nanoparticles of polymer-associated active ingredient can be either a dispersion in a common solvent or a dried solid. The common solvent is typically one that is capable of swelling the polymer nanoparticles as well as dissolving the active ingredient at a concentration of at least about 10 mg/mL, e.g., at least about 20 mg/mL. The polymer nanoparticles are typically dispersed in the common solvent at a concentration of at least about 10 mg/mL, e.g., at least about 20 mg/mL. In some embodiments, the common solvent is an alcohol (either long or short chain), preferably methanol or ethanol. In some embodiments the common solvent is selected from alkenes, alkanes, alkynes, phenols, hydrocarbons, chlorinated hydrocarbons, ketones, and ethers. In some embodiments, the common solvent is a mixture of two or more different solvents that are miscible or partially miscible with each other. Some or all of the common solvent is removed from the dispersion of pre-formed polymer nanoparticles and active ingredients by either direct evaporation or evaporation under reduced pressure. The dispersion can be dried by a range of processes known by a practitioner of the art such as lyophilization (freeze-drying), spray-drying, tray-drying, evaporation, jet drying, or other methods to obtain the nanoparticles of polymers-associated with active ingredients. In general, the amount of solvent that is removed from the dispersion described above will depend on the final type of formulation that is desired. This is illustrated further in the Examples and in the general description of specific formulations.

In some instances the solids content (including both the polymer and active ingredient components as well as other solid form formulating agents) of the formulation is between about 1 and about 98 weight % of the total formulation. In some embodiments, the solids content of the formulation is between about 1 and about 90 weight % of the total formulation. In some embodiments, the solids content of the formulation is between about 1 and about 75 weight % of the total formulation. In some embodiments, the solids content of the formulation is between about 1 and about 50 weight % of the total formulation. In some embodiments, the solids content of the formulation is between about 1 and about 30 weight % of the total formulation. In some embodiments, the solids content of the formulation is between about 1 and about 25 weight % of the total formulation. In some embodiments, the solids content of the formulation is between about 1 and about 10 weight % of the total formulation. In some embodiments, the solids content of the formulation is between about 10 and about 25 weight % of the total formulation. In some embodiments, the solids content of the formulation is between about 10 and about 30 weight % of the total formulation. In some embodiments, the solids content of the formulation is between about 10 and about 50 weight % of the total formulation. In some embodiments, the solids content of the formulation is between about 10 and about 75 weight % of the total formulation. In some embodiments, the solids content of the formulation is between about 10 and about 90 weight % of the total formulation. In some embodiments, the solids content of the formulation is between about 10 and about 98 weight % of the total formulation. In some embodiments, the solids content of the formulation is between about 25 and about 50 weight % of the total formulation. In some embodiments, the solids content of the formulation is between about 25 and about 75 weight % of the total formulation. In some embodiments, the solids content of the formulation is between about 25 and about 90 weight % of the total formulation. In some embodiments, the solids content of the formulation is between about 30 and about 98 weight % of the total formulation. In some embodiments, the solids content of the formulation is between about 50 and about 90 weight % of the total formulation. In some embodiments, the solids content of the formulation is between about 50 and about 98 weight % of the total formulation. In some embodiments, the solids content of the formulation is between about 75 and about 90 weight % of the total formulation. In some embodiments, the solids content of the formulation is between about 75 and about 98 weight % of the total formulation.

Formulating Agents

As used herein, the term "formulating agent" refers to any other material used in the formulation other than the nanoparticles of polymer-associated active ingredient. Formulating agents can include, but are not limited to, compounds that can act as a dispersants or wetting agents, inert fillers, solvents, surfactants, anti-freezing agents, anti-settling agents or thickeners, disintegrants, and preservatives.

In some embodiments, a formulation may include a dispersant or wetting agent or both. In some embodiments the same compound may act as both a dispersant and a wetting agent. A dispersant is a compound that helps the nanoparticles (or aggregates of nanoparticles) disperse in water. Without wishing to be bound by any theory, dispersants are thought to achieve this result by absorbing on to the surface of the nanoparticles and thereby limiting re-aggregation. Wetting agents increase the spreading or penetration power of a liquid when placed onto the substrate (e.g., leaf). Without wishing to be bound by any theory, wetting agents are thought to achieve this result by reducing the interfacial tension between the liquid and the substrate surface.

In a similar manner, some formulating agents may demonstrate multiple functionality. The categories and listings of specific agents below are not mutually exclusive. For example, fumed silica, described below in the thickener/anti-settling agent and anti-caking agent sections, is typically used for these functions. In some embodiments, however, fumed silica demonstrates the functionality of a wetting agent and/or dispersant. Specific formulating agents listed below are categorized based on their primary functionality, however, it is to be understood that particular formulating agents may exhibit multiple functions. Certain formulation ingredients display multiple functionalities and synergies with other formulating agents and may demonstrate superior properties in a particular formulation but not in another formulation.

In some embodiments, a dispersant or wetting agent is selected from organosilicones (e.g., SYLGARD 309 from Dow Corning Corporation or SILWET L77 from Union Carbide Corporation) including polyalkylene oxide modified polydimethylsiloxane (SILWET L7607 from Union Carbide Corporation), methylated seed oil, and ethylated seed oil (e.g., SCOIL from Agsco or HASTEN from Wilfarm), alkylpolyoxyethylene ethers (e.g., ACTIVATOR 90), alkylarylalolates (e.g., APSA 20), alkylphenol ethoxylate and alcohol alkoxylate surfactants (e.g., products sold by Huntsman), fatty acid, fatty ester and fatty amine ethoxylates (e.g., products sold by Huntsman), products sold by Cognis such as sorbitan and ethoxylated sorbitan esters, ethoxylated vegetable oils, alkyl, glycol and glycerol esters and glycol ethers, tristyrylphenol ethoxylates, anionic surfactants such as sulfonates, such as sulfosuccinates, alkylaryl sulfonates, alkyl naphthalene sulfonates (e.g., products sold by Adjuvants Unlimited), calcium alkyl benzene sulfonates, and phosphate esters (e.g., products sold by Huntsman Chemical or BASF), as salts of sodium, potassium, ammonium, magnesium, triethanolamine (TEA), etc.

Other specific examples of the above sulfates include ammonium lauryl sulfate, magnesium lauryl sulfate, sodium 2-ethyl-hexyl sulfate, sodium actyl sulfate, sodium oleyl sulfate, sodium tridecyl sulfate, triethanolamine lauryl sulfate, ammonium linear alcohol, ether sulfate ammonium nonylphenol ether sulfate, and ammonium monoxynol-4-sulfate. Other examples of dispersants and wetting agents include, sulfosuccinamates, disodium N-octadecylsulfo-succinamate; tetrasodium N-(1,2-dicarboxyethyl)-N-octadecylsulfo-succinamate; diamyl ester of sodium sulfosuccinic acid; dihexyl ester of sodium sulfosuccinic acid; and dioctyl esters of sodium sulfosuccinic acid; dihexyl ester of sodium sulfosuccinic acid; and dioctyl esters of sodium sulfosuccinic acid; castor oil and fatty amine ethoxylates, including sodium, potassium, magnesium or ammonium salts thereof. Dispersants and wetting agents also include natural emulsifiers, such as lecithin, fatty acids (including sodium, potassium or ammonium salts thereof) and ethanolamides and glycerides of fatty acids, such as coconut diethanolamide and coconut mono- and diglycerides. Dispersants and wetting agents also include sodium polycarboxylate (commercially available as Geropon TA/72); sodium salt of naphthalene sulfonate condensate (commercially available as Morwet (D425, D809, D390, EFW); calcium naphthalene sulfonates (commercially available as DAXAD 19LCAD); sodium lignosulfonates and modified sodium lignosulfonates; aliphatic alcohol ethoxylates; ethoxylated tridecyl alcohols (commercially available as Rhodasurf (BC420, BC610, BC720, BC 840); Ethoxylated tristeryl phenols (commercially available as Soprophor BSU); sodium methyl oleyl taurate (commercially available as Geropon T-77); tristyrylphenol ethoxylates and esters; ethylene oxide-propylene oxide block copolymers; non-ionic copolymers (e.g., commercially available Atlox 4913), non-ionic block copolymers (commercially available as Atlox 4912). Examples of dispersants and wetting agents include, but are not limited to, sodium dodecylbenzene sulfonate; N-oleyl N-methyl taurate; 1,4-dioctoxy-1,4-dioxo-butane-2-sulfonic acid; sodium lauryl sulphate; sodium dioctyl sulphosuccinate; aliphatic alcohol ethoxylates; nonylphenol ethoxylates. Dispersants and wetting agents also include sodium taurates; and sodium or ammonium salts of maleic anhydride copolymers, lignosulfonic acid formulations or condensed sulfonate sodium, potassium, magnesium or ammonium salts, polyvinylpyrrolidone (available commercially as POLYPLASDONE XL-10 from International Specialty Products or as KOLLIDON C1

M-10 from BASF Corporation), polyvinyl alcohols, modified or unmodified starches, methylcellulose, hydroxyethyl or hydroxypropyl methylcellulose, carboxymethyl methylcellulose, or combinations, such as a mixture of either lignosulfonic acid formulations or condensed sulfonate sodium, potassium, magnesium or ammonium salts with polyvinylpyrrolidone (PVP).

In some embodiments, the dispersants and wetting agents can combine to make up between about 1 and about 30 weight % of the formulation. For example, dispersants and wetting agents can make up between about 1 and about 20 weight %, about 1 and about 10 weight %, between about 1 and about 5 weight %, between about 1 and about 3 weight %, between about 2 and about 30 weight %, between about 2 and about 20 weight %, between about 2 and about 10 weight %, between about 3 and about 30 weight %, between about 3 and about 20 weight %, between about 3 and about 10 weight %, between about 3 and about 5 weight %, between about 5 and about 30 weight %, between about 5 and about 20 weight %, between about 5 and about 10 weight % of the formulation. In some embodiments, dispersants or wetting agents can make up between about 0.1 and 1 weight % of the formulation.

In some embodiments, a formulation may include an inert filler. For example, an inert filler may be included to produce or promote cohesion in forming a wettable granule formulation. An inert filler may also be included to give the formulation a certain active loading, density, or other similar physical properties. Non limiting examples of inert fillers that may be used in a formulation include bentonite clay, carbohydrates, proteins, lipids synthetic polymers, glycolipids, glycoproteins, lipoproteins, lignin, lignin derivatives, and combinations thereof. In a preferred embodiment the inert filler is a lignin derivative and is optionally calcium lignosulfonate. In some embodiments, the inert filler is selected from the group consisting of: monosaccharides, disaccharides, oligosaccharides, polysaccharides and combinations thereof. Specific carbohydrate inert fillers illustratively include glucose, mannose, fructose, galactose, sucrose, lactose, maltose, xylose, arabinose, trehalose and mixtures thereof such as corn syrup; sugar alcohols including: sorbitol, xylitol, ribitol, mannitol, galactitol, fucitol, iditol, inositol, volemitol, isomalt, maltitol, lactitol, polyglycitol; celluloses such as carboxymethylcellulose, ethylcellulose, hydroxyethylcellulose, hydroxy-methylethylcellulose, hydroxyethylpropylcellulose, methylhydroxyethylcellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; vegetable oils such as corn, soybean, peanut, canola, olive and cotton seed; complex organic substances such as lignin and nitrolignin; derivatives of lignin such as lignosulfonate salts illustratively including calcium lignosulfonate and sodium lignosulfonate and complex carbohydrate-based formulations containing organic and inorganic ingredients such as molasses. Suitable protein inert fillers illustratively include soy extract, zein, protamine, collagen, and casein. Inert fillers operative herein also include synthetic organic polymers capable of promoting or producing cohesion of particle components and such inert fillers illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex.

In some embodiments, a formulation contains between about 1 and about 90 weight % inert filler, e.g., between about 1 and about 80 weight %, between about 1 and about 60 weight %, between about 1 and about 40 weight %, between about 1 and about 25 weight %, between about 1 and about 10 weight %, between about 10 and about 90 weight %, between about 10 and about 80 weight %, between about 10 and about 60 weight %, between about 10 and about 40 weight %, between about 10 and about 25 weight %, between about 25 and about 90 weight %, between about 25 and about 80 weight %, between about 25 and about 60 weight %, between about 25 and about 40 weight %, between about 40 and about 90 weight %, between about 40 and about 80 weight %, or between about 60 and about 90 weight %.

In some embodiments, a formulation may include a solvent or a mixture of solvents that can be used to assist in controlling the solubility of the active ingredient itself, the nanoparticles of polymer-associated active ingredients, or other components of the formulation. For example, the solvent can be chosen from water, alcohols, alkenes, alkanes, alkynes, phenols, hydrocarbons, chlorinated hydrocarbons, ketones, ethers, and mixtures thereof. In some embodiments, the formulation contains a solvent or a mixture of solvents that makes up about 0.1 to about 90 weight % of the formulation. In some embodiments, a formulation contains between about 0.1 and about 90 weight % solvent, e.g., between about 1 and about 80 weight %, between about 1 and about 60 weight %, between about 1 and about 40 weight %, between about 1 and about 25 weight %, between about 1 and about 10 weight %, between about 10 and about 90 weight %, between about 10 and about 80 weight %, between about 10 and about 60 weight %, between about 10 and about 40 weight %, between about 10 and about 25 weight %, between about 25 and about 90 weight %, between about 25 and about 80 weight %, between about 25 and about 60 weight %, between about 25 and about 40 weight %, between about 40 and about 90 weight %, between about 40 and about 80 weight %, between about 60 and about 90 weight %, between about 0.1 and about 10 weight %, between about 0.1 and about 5 weight %, between about 0.1 and about 3 weight %, between about 0.1 and about 1 weight %, between about 0.5 and about 20 weight %, 0 between about 0.5 and about 10 weight %, between about 0.5 and about 5 weight %, between about 0.5 and about 3 weight %, between about 0.5 and about 1 weight %, between about 1 and about 20 weight %, between about 1 and about 10 weight %, between about 1 and about 5 weight %, between about 1 and about 3 weight %, between about 5 and about 20 weight %, between about 5 and about 10 weight %, between about 10 or about 20 weight %.

In some embodiments, a formulation may include a surfactant. When included in formulations, surfactants can function as wetting agents, dispersants, emulsifying agents, solubilizing agents and bioenhancing agents. Without limitation, particular surfactants may be anionic surfactants, cationic surfactants, nonionic surfactants, amphoteric surfactants, silicone surfactants (e.g., Silwet L77), and fluorosurfactants. Exemplary anionic surfactants include alkylbenzene sulfonates, alkyl sulfonates and ethoxylates, sulfosuccinates, phosphate esters, taurates, alkylnaphthalene sulfonates and polymers lignosulfonates. Exemplary nonionic surfactants include alkylphenol ethoxylates, aliphatic alcohol ethoxylates, aliphatic alkylamine ethoxylates, amine alkoxylates, sorbitan esters and their ethoxylates, castor oil ethoxylates, ethylene oxide/propylene oxide copolymers and polymeric surfactants. In some embodiments, surfactants can make up between about 0.1 and about 20 weight % of the formulation, e.g., between about 0.1-15 weight %, between about 0.1 and about 10 weight %, between about 0.1 and about 8 weight %, between about 0.1 and about 6 weight %, between about 0.1 and about 4 weight %, between about 1-15 weight %, between about 1 and about 10 weight %, between about 1 and about 8 weight %, between about 1 and about 6 weight %, between about 1 and about 4 weight %, between about 3 and about 20 weight %, between about 3 and about 15 weight %, between about 3 and about 10 weight %, between about 3 and about 8 weight %, between about 3 and about 6 weight %, between about 5 and about 15 weight %, between about 5 and about 10 weight %, between about 5 and about 8 weight %, or between about 10 and about 15 weight %. In some embodiments, a surfactant (e.g., a non-ionic surfactant) may be added to a formulation by the end user, e.g., in a spray tank. Indeed, when a formulation is added to the spray tank it becomes diluted and, in some embodiments, it may be advantageous to add additional surfactant in order to maintain the nanoparticles in dispersed form.

In some embodiments, a formulation may include an anti-settling agent or thickener that can help provide stability to a liquid formulation or modify the rheology of the formulation. Examples of anti-settling agents or thickeners include, but are not limited to, guar gum; locust bean gum; xanthan gum; carrageenan; alginates; methyl cellulose; sodium carboxymethyl cellulose; hydroxyethyl cellulose; modified starches; polysaccharides and other modified polysaccharides; polyvinyl alcohol; glycerol alkyd resins such as Latron B-1956 from Rohm & Haas Co., plant oil based materials (e.g., cocodithalymide) with emulsifiers; polymeric terpenes; microcrystalline cellulose; methacrylates; poly(vinylpyrrolidone), syrups, polyethylene oxide, and fumed silica (e.g., Aerosil 380). In some embodiments, anti-settling agents or thickeners can make up between about 0.05 and about 10 weight % of the formulation, e.g., about 0.05 to about 5 weight %, about 0.05 to about 3 weight %, about 0.05 to about 1 weight %, about 0.05 to about 0.5 weight %, about 0.05 to about 0.1 weight %, about 0.1 to about 5 weight %, about 0.1 to about 3 weight %, about 0.1 to about 1 weight %, about 0.1 to about 0.5 weight %, about 0.5 to about 5 weight %, about 0.5 to about 3 weight %, about 0.5 to about 1 weight %, about 1 to about 10 weight %, about 1 to about 5 weight %, or about 1 to about 3 weight %. In some embodiments, it is explicitly contemplated that a formulation of the present disclosure does not include a compound whose primary function is to act as an anti-settling or thickener. In some embodiments, compounds included in a formulation may have some anti-settling or thickening functionality, in addition to other, primary functionality, so anti-settling or thickening functionality is not a necessary condition for exclusion, however, formulation agents used primarily or exclusively as anti-settling agents or thickeners may be expressly omitted from the formulations.

In some embodiments, a formulation may include one or more preservatives that prevent microbial or fungal degradation of the product during storage. Examples of preservatives include but are not limited to, tocopherol, ascorbyl palmitate, propyl gallate, butylated hydroxyanisole (BHA), butylated hydroxytoluene (BHT), propionic acid and its sodium salt; sorbic acid and its sodium or potassium salts; benzoic acid and its sodium salt; p-hydroxy benzoic acid sodium salt; methyl p-hydroxy benzoate; 1,2-benzisothiazalin-3-one, and combinations thereof. In some embodiments, preservatives can make up about 0.01 to about 0.2 weight % of the formulation, e.g., between about 0.01 and about 0.1 weight %, between about 0.01 and about 0.05 weight %, between about 0.01 and about 0.02 weight %, between about 0.02 and about 0.2 weight %, between about 0.02 and about 0.1 weight %, between about 0.02 and about 0.05 weight %, between about 0.05 and about 0.2 weight %, between about 0.05 and about 0.1 weight %, or between about 0.1 and about 0.2 weight %.

In some embodiments, a formulation may include anti-freezing agents, anti-foaming agents, and/or anti-caking agents that help stabilize the formulation against freezing during storage, foaming during use, or caking during storage. Examples of anti-freezing agents include, but are not limited to, ethylene glycol, propylene glycol, and urea. In certain embodiment a formulation may include between about 0.5 and about 10 weight % anti-freezing agents, e.g., between about 0.5 and about 5 weight %, between about 0.5 and about 3 weight %, between about 0.5 and about 2 weight %, between about 0.5 and about 1 weight %, between about 1 and about 10 weight %, between about 1 and about 5 weight %, between about 1 and about 3 weight %, between about 1 and about 2 weight %, between about 2 and about 10 weight %, between about 3 and about 10 weight %, or between about 5 and about 10 weight %.

Examples of anti-foaming agents include, but are not limited to, silicone based anti-foaming agents (e.g., aqueous emulsions of dimethyl polysiloxane, FG-10 from Dow-Corning®, Trans 10A from Trans-Chemo Inc.), and non-silicone based anti-foaming agents such as octanol, nonanol, and silica. In some embodiments a formulation may include between about 0.05 and about 5 weight % of anti-foaming agents, e.g., between about 0.05 and about 0.5 weight %, between about 0.05 and about 1 weight %, between about 0.05 and about 0.2 weight %, between about 0.1 and about 0.2 weight %, between about 0.1 and about 0.5 weight %, between about 0.1 and about 1 weight %, or between about 0.2 and about 1 weight %.

Examples of anti-caking agents include sodium or ammonium phosphates, sodium carbonate or bicarbonate, sodium acetate, sodium metasilicate, magnesium or zinc sulfates, magnesium hydroxide (all optionally as hydrates), sodium alkylsulfosuccinates, silicious compounds, magnesium compounds, C10-C22 fatty acid polyvalent metal salt compounds, and the like. Illustrative of anti-caking ingredients are attapulgite clay, kieselguhr, silica aerogel, silica xerogel, perlite, talc, vermiculite, sodium aluminosilicate, zirconium oxychloride, starch, sodium or potassium phthalate, calcium silicate, calcium phosphate, calcium nitride, aluminum nitride, copper oxide, magnesium carbonate, magnesium silicate, magnesium nitride, magnesium phosphate, magnesium oxide, magnesium nitrate, magnesium sulfate, magnesium chloride, and the magnesium and aluminum salts of C10-C22 fatty acids such as palmitic acid, stearic acid and oleic acid. Anti-caking agents also include refined kaolin clay, amorphous precipitated silica dioxide, such as HI SIL 233 available from PPG Industries, refined clay, such as HUBERSIL available from Huber Chemical Company, or fumed silica (e.g., Aerosil 380) In some embodiments, a formulation may include between about 0.05 and about 10 weight % anti-caking agents, e.g., between about 0.05 to 5 weight %, between about 0.05 and about 3 weight %, between about 0.05 and about 2 weight %, between about 0.05 and about 1 weight %, between about 0.05 and about 0.5 weight %, between about 0.05 and about 0.1 weight %, between about 0.1 and about 5 weight %, between about 0.1 and about 3 weight %, between about 0.1 and about 2 weight %, between about 0.1 and about 1 weight %, between about 0.1 and about 0.5 weight %, between about 0.5 and about 5 weight %, between about 0.5 and about 3 weight %, between about 0.5 and about 2 weight %, between about 0.5 and about 1 weight %, between about 1 to 3 weight %, between about 1 to 10 weight %, or between about 1 and about 5 weight %.

In some embodiments, a formulation may include a UV-blocking compound that can help protect the active ingredient from degradation due to UV irradiation. Examples of UV-blocking compounds include ingredients commonly found in sunscreens such as benzophenones, benzotriazoles, homosalates, alkyl cinnamates, salicylates such as octyl salicylate, dibenzoylmethanes, anthranilates, methylbenzylidenes, octyl triazones, 2-phenylbenzimidazole-5-sulfonic acid, octocrylene, triazines, cinnamates, cyanoacrylates, dicyano ethylenes, etocrilene, drometrizole trisiloxane, bisethylhexyloxyphenol methoxyphenol triazine, drometrizole, dioctyl butamido triazone, terephthalylidene dicamphor sulfonic acid and para-aminobenzoates as well as ester derivatives thereof, UV-absorbing metal oxides such as titanium dioxide, zinc oxide, and cerium oxide, and nickel organic compounds such as nickel bis(octylphenol)sulfide, etc. Additional examples of each of these classes of UV-blockers may be found in Kirk-Othmer, Encyclopedia of Chemical Technology. In some embodiments, a formulation may include between about 0.01 and about 2 weight % UV-blockers, e.g., between about 0.01 and about 1 weight %, between about 0.01 and about 0.5 weight %, between about 0.01 and about 0.2 weight %, between about 0.01 and about 0.1 weight %, between about 0.01 and about 0.05 weight %, between about 0.05 weight % and about 1 weight %, between about 0.05 and about 0.5 weight %, between about 0.05 and about 0.2 weight %, between about 0.05 and about 0.1 weight %, between about 0.1 and about 1 weight %, between about 0.1 and about 0.5 weight %, between about 0.1 and about 0.2 weight %, between about 0.2 and about 1 weight %, between about 0.2 and about 0.5 weight %, or between about 0.5 and about 1 weight %. In some embodiments, it is explicitly contemplated that a formulation of the present disclosure does not include a compound whose primary function is to act as a UV-blocker. In some embodiments, compounds included in a formulation may have some UV-blocking functionality, in addition to other, primary functionality, so UV-blocking is not a necessary condition for exclusion, however, formulation agents used primarily or exclusively as UV-blockers may be expressly omitted from the formulations.

In some embodiments, a formulation may include a disintegrant that can help a solid formulation break apart when added to water. Examples of suitable disintegrants include cross-linked polyvinyl pyrrolidone, modified cellulose gum, pregelatinized starch, cornstarch, modified corn starch (e.g., STARCH 1500) and sodium carboxymethyl starch (e.g., EXPLOTAB or PRIMOJEL), microcrystalline cellulose, sodium starch glycolate, sodium carboxymethyl cellulose, carmellose, carmellose calcium, carmellose sodium, croscarmellose sodium, carmellose calcium, carboxymethylstarch sodium, low-substituted hydroxypropyl cellulose, hydroxypropyl methylcellulose, hydroxypropyl cellulose, soy polysaccharides (e.g., EMCOSOY), alkylcelullose, hydroxyalkylcellulose, alginates (e.g., SATIALGINE), dextrans and poly(alkylene oxide) and an effervescent couple (e.g., citric or ascorbic acid plus bicarbonate), lactose, anhydrous dibasic calcium phosphate, dibasic calcium phosphate, magnesium aluminometasilicate, synthesized hydrotalcite, silicic anhydride and synthesized aluminum silicate. In some embodiments disintegrants can make up between about 1 and about 20 weight % of the formulation, e.g., between about 1 and about 15 weight %, between about 1 and about 10 weight %, between about 1 and about 8 weight %, between about 1 and about 6 weight %, between about 1 and about 4 weight %, between about 3 and about 20 weight %, between about 3 and about 15 weight %, between about 3 and about 10 weight %, between about 3 and about 8 weight %, between about 3 and about 6 weight %, between about 5 and about 15 weight %, between about 5 and about 10 weight %, between about 5 and about 8 weight %, or between about 10 and about 15 weight %.

Formulations

As described above, the nanoparticles of polymer-associated active ingredient can be formulated into different types of formulations for different applications. For example, the types of formulations can include wettable granules, wettable powders, and high solid liquid suspensions. Furthermore, as discussed above, formulation agents can include, but are not limited to dispersants, wetting agents, surfactants, anti-settling agents or thickeners, preservatives, anti-freezing agents, anti-foaming agents, anti-caking agents, inert fillers, and UV-blockers.

In some embodiments, a dispersion of polymer nanoparticles and active ingredient in a common solvent is dried (e.g., spray dried) to form a solid containing nanoparticles (optionally in aggregate form) of polymer-associated active ingredients. The spray dried solid can then be used as is or incorporated into a formulation containing other formulating agents to make a wettable granule (WG), wettable powder (WP), or a high solids liquid suspension (HSLS).

In some embodiments, active ingredient is milled in the presence of pre-formed polymer nanoparticles to form a solid containing nanoparticles (optionally in aggregate form) of polymer-associated active ingredients. The solid can then be used as is or incorporated into a formulation containing other formulating agents to make a wettable granule (WG), wettable powder (WP), or a high solids liquid suspension (HSLS). In some embodiments, the milling step may be performed in the presence of one or more formulating agents. In some embodiments, the milling step may be performed in the presence of an aqueous phase.

Wettable Powder (WP)

In some embodiments, the dried solid can be made into a formulation that is a wettable powder (WP). In some embodiments, a WP formulation comprising nanoparticles of polymer-associated active ingredients (optionally in aggregate form) can be made from a dried (e.g., spray dried, freeze dried, etc.) dispersion of polymer nanoparticles and active ingredient. In some embodiments, a WP formulation comprising nanoparticles of polymer-associated active ingredients (optionally in aggregate form) can be made from a milled solid comprising polymer nanoparticles of active ingredient. In some embodiments, a WP is made by mixing the dried solid with a dispersant and/or a wetting agent. In some embodiments, a WP is made by mixing the dried solid or milled solid with a dispersant and/or a wetting agent. In some embodiments, a WP is made by mixing the dried or milled solid with a dispersant and a wetting agent. In some embodiments, the formulation of the final WP can be (by weight): up to about 98% nanoparticles of polymer-associated active ingredients (including both the active ingredient and the polymer, optionally in aggregate form). In some embodiments, the WP formulation includes (by weight): 0-5% dispersant, 0-5% wetting agent, 5-98% nanoparticles of polymer-associated active ingredients (optionally in aggregate form), and inert filler to 100%. In some embodiments, the formulation of the final WP can be (by weight): 0.5-5% dispersant, 0.5%-5% wetting agent, 5-98% nanoparticles of polymer-associated active ingredients (optionally in aggregate form), and inert filler to 100%. As described above in the Formulating Agents and Nanoparticles of polymer-associated active ingredient sections, a wide variety of formulating agent(s) and various concentrations of nanoparticles (including aggregates), wetting agents, dispersants, fillers and other formulating agents can be used to prepare exemplary formulations, e.g. wettable granules.

In some embodiments, the formulation of the final WP can be (by weight): 0.5-5% dispersant, 0.5%-5% wetting agent, 0.1-10% thickener (e.g., fumed silica which, as noted above may serve multiple functions, and/or xanthan gum), 5-98% nanoparticles of polymer-associated active ingredients (optionally in aggregate form). As described above in the Formulating Agents section, a wide variety of formulating agent(s) and various concentrations of wetting agents, dispersants, fillers and other formulating agents can be used to prepare exemplary formulations, e.g. wettable powders.

In some exemplary embodiments, a WP formulation comprising nanoparticles of polymer-associated active ingredients (optionally in aggregate form) may be made from a dispersion of polymer nanoparticles and active ingredient in a common solvent, preferably methanol. In some embodiments, a WP formulation can be made by adding the dispersion in common solvent into an aqueous solution containing a wetting agent (e.g., a surfactant such as sodium dodecylbenzene sulfonate) and/or a dispersant (e.g., a lignosulfonate such as Reax 88B, etc.) and optionally an inert filler (e.g., lactose), and then drying (e.g., freeze drying, spray drying, etc.) the resulting mixture to from a solid powder. In some embodiments, polyvinyl alcohol) is added to the solution prior to drying. In some embodiments a WP can be made using a wetting agent (e.g., a surfactant such as sodium dodecylbenzene sulfonate or dioctyl sulfosuccinate sodium salt) and a dispersant (e.g., a lignosulfonate such as Reax 88B, etc.).

In some exemplary embodiments, also described in more detail below, the polymer nanoparticles are made from a co-polymer of methacrylic acid and ethyl acrylate at about a 90:10 mass ratio. In some embodiments, the polymer nanoparticles are dispersed in a common solvent, preferably at a concentration of about 50 mg/mL. In some embodiments, the concentration of active ingredient is in the range between about 20 mg/mL to about 100 mg/mL. In some embodiments, the common solvent contains a wetting agent and/or dispersant as well. In some embodiments, the polymer nanoparticles are made from a co-polymer of methacrylic acid and (ethylene glycol)methyl ether methacrylate at about at a mass ratio of 7:3. In some embodiments, the polymer nanoparticles are made from a polymer of acrylic acid. In some embodiments, the polymer nanoparticles are made from a co-polymer of acrylic acid and styrene at about a 90:10 mass ratio. As described above in the Nanoparticles of polymer-associated active ingredient section, many ratios of co-polymer constituents can be used.

In some embodiments, the dispersion of polymer nanoparticles and active ingredient is then slowly added into a vessel containing a second solvent, preferably water. In some embodiments, the second solvent is at least 20 times larger in volume than the common solvent containing the polymer nanoparticles and active ingredient. In some embodiments, the second solvent contains a dispersant, preferably a lignosulfonate such as Reax 88B and/or a wetting agent, preferably a surfactant such as sodium dodecylbenzene sulfonate. In some embodiments a WP can be made using a wetting agent (e.g., a surfactant such as sodium dodecylbenzene sulfonate or dioctyl sulfosuccinate sodium salt) and a dispersant (e.g., a lignosulfonate such as Reax 88B, etc.).

In some embodiments, after the dispersion of polymer nanoparticles and active ingredient in a common solvent is mixed with a second solvent containing dispersant and/or wetting agent, the final mixture is dried (e.g., freeze dried) to obtain a solid powdered formulation containing nanoparticles of polymer-associated active ingredients (optionally in aggregate form). Optionally, the pH of the final mixture can be adjusted (e.g., by addition of acid or base solutions) as needed. Further, additional formulation agents (e.g., PVA solution) can also be added to the final mixture prior to drying.

High Solids Liquid Suspension (HSLS)

One type of formulation that can be utilized according to the disclosure is a high solids liquid suspension. As described, such a formulation is generally characterized in that it is a liquid formulation that contains at least nanoparticles of polymer nanoparticles associated with active ingredient (includes potentially aggregates of the same). HSLS formulations most closely resemble suspension concentrate (SC) formulations and can be considered a subcategory SCs incorporating polymer nanoparticles which are associated or encapsulate the active ingredient and have a smaller average particle size.

In some embodiments, the formulation of the HSLS can be (by weight): between about 5 and about 80% nanoparticles of polymer-associated active ingredients (including both polymer and active ingredient, optionally in aggregate form), 0.5 and about 5% wetting agent and/or dispersant, between about 1 and about 10% anti-freezing agent, between about 0.1 and about 2% UV blocker, between about 0.1 and about 10% anti-foaming agent, between about 0.01 and about 0.1% preservative and water up to 100% As described above in the Formulating Agents and Nanoparticles of polymer-associated active ingredient sections, a wide variety of formulating agent(s) and various concentrations of nanoparticles (including aggregates), wetting agents, dispersants, fillers and other formulating agents can be used to prepare exemplary formulations, e.g., a HSLS.

In some embodiments, the formulation of the HSLS can be (by weight): between about 1 and about 75% nanoparticles of polymer-associated active ingredients (including both polymer and active ingredient, optionally in aggregate form), 0.5 and about 5% wetting agent and/or dispersant, between about 1 and about 10% anti-freezing agent, between about 0.01 and about 2% UV blocker, between about 0.1 and about 10% anti-foaming agent, between about 0.01 and about 0.1% preservative, between about 0.1 and 4% surfactant, and water up to 100% As described above in the Formulating Agents and Nanoparticles of polymer-associated active ingredient sections, a wide variety of formulating agent(s) and various concentrations of nanoparticles (including aggregates), wetting agents, dispersants, fillers and other formulating agents can be used to prepare exemplary formulations, e.g., a HSLS.

In some exemplary embodiments, described in more detail below, the polymer nanoparticles are made from a co-polymer of methacrylic acid and styrene at about a 75:25 mass ratio. In some embodiments, the polymer nanoparticles are made from a co-polymer of methacrylic acid, styrene and sodium acrylamide-2-methylpropanesulfonate ("NaAMPS") with varying mass ratios between the three monomer components (e.g., 10-30:10-30:40-80, for methacrylic acid, styrene and sodium acrylamide-2-2-methylpropanesulfonate monomers, respectively). In some embodiments, the polymer nanoparticles are dispersed in the common solvent, preferably at a concentration of up to about 20 mg/mL. In some embodiments, the active ingredient is abamectin and is mixed into the nanoparticle dispersion at a concentration of up to about 20 mg/mL. As described above in the Nanoparticles of polymer-associated active ingredient section, many ratios of co-polymer constituents can be used.

In some embodiments, the dispersion of polymer nanoparticles and active ingredient in a common solvent is slowly added into a vessel containing a second solvent, preferably water. In some embodiments, the second solvent is at least 20 times larger in volume than the common solvent containing the polymer nanoparticles and active ingredient. In some embodiments, the second solvent contains a dispersant and/or a wetting agent, preferably a non-ionic surfactant such as Geropon 77 and/or TA-72. In some embodiments a HSLS can be made using a wetting agent and a dispersant.

In some embodiments, the HSLS formulations of current disclosure have an active ingredient content of about 5 to about 40% by weight, e.g., about 5-about 40%, about 5-about 35%, about 5-about 30%, about 5-about 25%, about 5-about 20%, about 5-about 15%, about 5-about 10%, about 10-about 40%, about 10-about 35%, about 10-about 30%, about 10-about 25%, about 10-about 20%, about 10-about 15%, about 15-about 40%, about 15-about 35%, about 15-about 30%, about 15-about 25%, about 15-about 20%, about 20-about 40%, about 20-about 35%, about 20-about 30%, about 20-about 25%, about 25-about 40%, about 25-about 35%, about 25-about 30%, about 30-about 40% or about 35-about 40%. As described above in the Nanoparticles of polymer-associated active ingredient section, many ratios of mectin or milbemycin to polymer can be used.

In some embodiments the HSLS formulations of current disclosure have an active ingredient content of about 5%, about 10%, about 15%, about 20%, about 25%, about 30%, about 35% or about 40% by weight.

Methods of Making HSLS—Generally

In some embodiments, a HSLS comprising nanoparticles of polymer-associated active ingredient (optionally in aggregate form) can be made from a dispersion of polymer nanoparticles and active ingredient in a common solvent or from a dried form of the dispersion (e.g., spray dried). In some embodiments, a HSLS formulation comprising nanoparticles of polymer-associated active ingredients (optionally in aggregate form) can be made from a milled solid comprising polymer nanoparticles of active ingredient.

Methods of Making HSLS—Milling Methods

In some embodiments, a HSLS formulation comprising nanoparticles of polymer-associated active ingredients (optionally in aggregate form) can be prepared via milling. Several exemplary methods and the resulting HSLS formulations are described below and in the Examples. In some embodiments, a solid formulation of nanoparticles of polymer-associate active ingredient (optionally in aggregate form), prepared as described in this disclosure (e.g., via milling, spray drying etc.) may be further milled in the presence of one or more formulating agents and water. In some embodiments a HSLS can be made by milling a solid formulation nanoparticles of polymer-associated active ingredients in the presence water and one more of an anti-freezing agent, (optionally more than one of) wetter(s) and/or dispersant(s), an antifoaming agent, a preservative, and a UV blocker. Further, in some embodiments, the active ingredient and polymer nanoparticles are milled together to produce nanoparticles of polymer-associated active ingredients, which may then be further milled according to the processes described below.

In some embodiments, the milling process is performed in separate phases (i.e., periods of time), with the optional addition of one or more formulating agent between each milling phase. One of ordinary skill in the art can adjust the length of each phase as is appropriate for a particular instance. In some embodiments, the contents of the milling vessel are cooled between one or more of milling phases (e.g., via placement of the milling jar in an ice bath). One of ordinary skill in the art can adjust the length of cooling period as is appropriate for a particular instance.

In some embodiments, a HSLS can be made by first milling a solid formulation of nanoparticles of polymer-associated active ingredients in the presence of (optionally more than one of) wetter(s) and/or dispersant(s) in one milling vessel for a certain amount of time (e.g., about 30 minutes-about 1 day), then this mixture is transferred to another milling vessel containing water and optionally one or more of an anti-freezing agent, additional wetter and/or dispersant, an anti-freezing agent, an antifoaming agent, a preservative, a UV blocker, and milling the components together. As described above in the Formulating Agents section, a wide variety of additional formulating agent(s) and various concentrations of wetting agents, dispersants, fillers and other formulating agents can be used in preparation of exemplary formulations.

And as in the embodiment described above in which nanoparticles of polymer-associated active ingredients are milled in a two milling vessel procedure, such a procedure can be used in preparing a HSLS from pre-formed polymer nanoparticles. In some embodiments such an HSLS can be made by first milling a solid formulation nanoparticles of polymer-associated active ingredients in the presence of (optionally more than one of) wetter(s) and/or dispersant(s) in one milling vessel for a certain amount of time (e.g., about 30 minutes-about 1 day), transferring the milled components to another milling vessel containing water and optionally one or more of an anti-freezing agent, additional wetter and/or dispersant, an anti-freezing agent, an antifoaming agent, a preservative and a UV blocker. In some embodiments, a HSLS is prepared by adding all of the HSLS components to a milling vessel and milling them together. In some embodiments a HSLS can be made by milling preformed polymer nanoparticles and active ingredient in the presence water and one more of an anti-freezing agent, (optionally more than one of) wetter(s) and/or dispersant(s), an antifoaming agent, a preservative, a UV blocker, and a surfactant.

Milling methods to produce HSLS formulations as described above may include any of those referred to in any other portion of the specification including the Examples below. Any type of mill noted in any portion of the specification may also be used to prepare HSLS formulations via milling.

Methods of Making HSLS—Mixing & Drying Methods

In some embodiments, a HSLS formulation is prepared without milling, but instead by mixing the components of the formulation. These methods may also include drying the formulations to increase the solids content of the formulation so that it is suitable as a HSLS. All of these methods are described in more detail below and exemplary methods are shown in the Examples.

In some embodiments, a HSLS formulation comprising nanoparticles of polymer-associated active ingredients (optionally in aggregate form) can be made from the dispersion of polymer nanoparticles and active ingredient in a common solvent, (e.g., methanol). In some embodiments, the dispersion is added to an aqueous solution containing a wetting agent(s) and a dispersant(s), an anti-freezing agent (and optionally a UV blocker and a preservative). The mixture is then concentrated by removing solvent, e.g., by drying, until the desired high solids formulation is attained.

In some exemplary embodiments, after the dispersion of polymer nanoparticles and active ingredient in a common solvent is mixed with a second solvent containing a wetting agent(s) and/or dispersant(s) and an anti-freezing agent (optionally with a UV blocker and a preservative), the final mixture is concentrated by removing most of the common solvent and second solvent until a final formulation with a target solids content (e.g., at least 60% solids) is obtained. In some embodiments, the method used to concentrate the solution is vacuum evaporation. In some embodiments, a second solvent containing a wetting agent and/or dispersant and an anti-freezing agent (optionally with a UV blocker and a preservative) are added after the mixture has already been concentrated. As described above in the Nanoparticles of polymer-associated active ingredient section, many ranges of solids content can be achieved.

In some embodiments, the dispersion of polymer nanoparticles and active ingredient in a common solvent is added to a second solvent to form a solution of nanoparticles of polymer-associated active ingredients (optionally in aggregate form). The second solvent is typically miscible with the common solvent and is usually water, but in some embodiments, the second solvent can also be a mixture of water with a third solvent, usually an alcohol, preferably methanol or ethanol. In some embodiments, the second solvent or mixture of solvents is only partially miscible with the common solvent. In some embodiments, the second solvent or mixture of solvents is not miscible with the common solvent.

Efficacy and Application

General Applications and Efficacy

As noted previously and in the Examples, in some embodiments, the disclosure provides formulations of mectin and milbemycin compounds that have either improved solubility, or stability properties. In some embodiments, the mectin or milbemycin formulations of the present disclosure demonstrate improved activity compared to commercial formulations of the same active ingredient, which suggests that they may be applied at lower effective rates in general applications.

In general, different mectins and milbemycins are typically applied at different effective rates between 10-400 grams of active ingredient (e.g. mectin and milbemycin) per hectare depending on the efficacy of the active ingredient (e.g., absolute potency of the active and retention at the site of activity), as well as conditions related to the crop being treated, leaf type, environmental conditions, the species infesting the crop, infestation levels, and other factors. As discussed above, improvements in the formulation according to the current disclosure, such as increased UV stability, physical retention at the site of action, improved water solubility can reduce the user rates. Some embodiments demonstrate improvements over typical commercial formulation, which suggests that lower rates of effective application could be used. In some embodiments, rates may range from between about 0.1 and about 400 g/hectare, preferably between about 0.1 and about 200 g/hectare, more preferably between about 0.1 and about 100 g/hectare, more preferably between about 0.1 and about 10 g/hectare or more preferably between about 0.1 and about 1 g/hectare. In some embodiments, rates may range from between about 1 g and about 400 g/hectare, preferably between about 1 and about 200 g/hectare, more preferably between about 1 and about 100 g/hectare, or more preferably between about 1 and about 10 g/hectare. In some embodiments, rates may be any of the rates or ranges of rates noted in any other portion of the specification.

General Application & Comparison to Current Commercial Formulations

In some embodiments, the disclosure provides methods of using formulations of nanoparticles of polymer-associated mectins and/or milbemycins. In some embodiments, the formulations are used to inoculate a target area of a plant. In some embodiments, the formulations are used to inoculate a part or several parts of the plant, e.g., the leaves, stem, roots, flowers, bark, buds, shoots, and/or sprouts.

In some embodiments, a formulation comprising nanoparticles of polymer-associated active ingredients and other formulating agents is added to water (e.g., in a spray tank) to make a dispersion that is about 10 to about 2,000 ppm in active ingredient. In some embodiments, the dispersion is about 10 to about 1,000 ppm, about 10 to about 500 ppm, about 10 to about 300 ppm, about 10 to about 200 ppm, about 10 to about 100 ppm, about 10 to about 50 ppm, about 10 to about 20 ppm, about 20 to about 2,000 ppm, about 20 to about 1,000 ppm, about 20 to about 500 ppm, about 20 to about 300 ppm, about 20 to about 200 ppm, about 20 to about 100 ppm, about 20 to about 50 ppm, about 50 to about 2,000 ppm, about 50 to about 1,000 ppm, about 50 to about 500 ppm, about 50 to about 300 ppm, about 50 to about 200 ppm, about 50 to about 100 ppm, about 100 to about 2,000 ppm, about 100 to about 1,000 ppm, about 100 to about 500 ppm, about 100 to about 300 ppm, about 100 to about 200 ppm, about 200 to about 2,000 ppm, about 200 to about 1,000 ppm, about 200 to about 500 ppm, about 200 to about 300 ppm, about 300 to about 2,000 ppm, about 300 to about 1,000 ppm, about 300 to about 500 ppm, about 500 to about 2,000 ppm, about 500 to about 1,000 ppm, about 1000 to about 2,000 ppm.

As used in the specification, inoculation of a plant with a formulation of the current disclosure may, in some embodiments, refer to inoculation of a plant with a dispersion (e.g., in water or an aqueous medium optionally further comprising other additive such as adjuvants, surfactants etc.) prepared from a formulation of the present disclosure as described above. It is to be understood that the term formulation may also encompass dispersions for applications as described (e.g., inoculation of a plant). It should also be understood that methods that describe the use of mectin and/or milbemycin formulations of the present disclosure e.g., "use of formulations of the present disclosure to inoculate a plant," "use of the formulations of the present disclosure to control pests" and the like, encompass the preparation of a dispersion of the active ingredient in water or an aqueous medium (optionally further comprising other additives such as adjuvants, surfactants etc.) for the purpose of inoculating a plant.

In some embodiments, a dispersion is produced and used to inoculate a plant with active ingredient at less than about 75% of a use rate listed on a label of a currently available commercial product of the same active ingredient. In some embodiments, a dispersion is produced to inoculate a plant with active ingredient at less than about 60% of a use rate listed on the label of a currently available commercial product of the same active ingredient. In some embodiments, a dispersion is produced to inoculate a plant with active ingredient at less than about 50% of a use rate listed on the label of a currently available commercial product of the same active ingredient. In some embodiments, a dispersion is produced to inoculate a plant with active ingredient at less than 40% of a use rate listed on the label of a currently available commercial product of the same active ingredient. In some embodiments, a dispersion is produced to inoculate a plant with active ingredient at less than 30% of a use rate listed on the label of a currently available commercial product of the same active ingredient. In some embodiments, a dispersion is produced to inoculate a plant with active ingredient at less than 25% of a use rate listed on the label of a currently available commercial product of the same active ingredient. In some embodiments, a dispersion is produced to inoculate a plant with active ingredient at less than 20% of a use rate listed on the label of a currently available commercial product of the same active ingredient. In some embodiments, a dispersion is produced to inoculate a plant with active ingredient at less than 10% of a use rate listed on the labels of a currently available commercial product of the same active ingredient. In some embodiments, a dispersion is produced to inoculate a plant with active ingredient at less than 5% of the use rate listed on a label of a currently available commercial product of the same active ingredient. In some embodiments, the mectin and/or milbemycin formulations of the present disclosure are used to inoculate a plant at an active ingredient use rate that is about 75%, about 60%, about 50%, about 40%, about 30%, about 25%, about 20% or about 10% of a use rate listed on the labels of currently available pesticide products. Pesticide labels can be referenced from commercial suppliers and are readily accessible and available.

In preferred embodiments, the formulations of the current disclosure may be used to control pests at an active ingredient use rate that is lower than the minimum rate of a range of rates listed on the label of a commercially available product. In some embodiments, formulations of the current disclosure may be used to control pests at an active ingredient use rate that is less than about 75%, less than about 60%, less than about 50%, less than about 40%, less than about 30%, less than about 25%, less than about 20% or less than about 10% of the minimum use rate of a range of rates listed on the label of a commercially available product.

Hard Water/Fertilizer Applications

As described below, most traditional formulations produce solid particles (floc) or a precipitate when mixed in with high salt, hard water or fertilizer solutions. Surprisingly, a dispersed solid formulation of a mectin and/or milbemycin (e.g., abamectin) of the current disclosure will be stable (e.g., components, difenoconazole and the salt, remained disperse, i.e., no visible sedimentation or floc) when mixed with a concentrated/high salt solution (e.g., hard water, buffer, concentrated fertilizer formulation) for at least 3 hours. This was true even for waters with ionic strength as high as 8000 ppm $Mg^{2+}$ (a.k.a. CIPAC "G" hard water). It is important to note that for such a mixture to be useful for the end user, the mixture should remain stable (i.e., no formation of sediments and/or flocs) within at least about 30-40 minutes—which is typically the time it takes for the mixture to be applied to the plant. It is surprising that the formulations of the present disclosure are stable in such high-salt conditions. Because the polymers that are used in the nanoparticles of the present disclosure are negatively charged, a practitioner of the art would expect the formulations of the present disclosure to flocculate when mixed with such a high amount of divalent salt. Without being limited by theory, it is believed that the increased stability of the formulations of the present disclosure arises from the use of nanoparticle polymers as the delivery system and that if standard non-nanoparticle polymers were used then flocculation would occur.

Traditional solid or liquid formulations are not stable under conditions of high ionic (i.e., a high salt solution) strength. Sources of increased ionic strength can include, for example, mineral ions that are present in the water that a formulation is dispersed in. For example, in many cases the water that is available to a farmer is taken from a high-salt ("hard water") source such as a well or aquifer. Water that a grower uses can be variably hard and is normally measured as $Ca^{2+}$ equivalents. Ranges of water salinity can be from ~0 ppm $Ca^{2+}$ equivalent (deionized water) to 8000 ppm $Ca^{2+}$ or more.

Other sources of increased ionic strength can include, for example, other chemicals or materials that dispersed in the spray tank water before or after the addition of the pesticide formulation. Examples of this include mineral additives such as micronutrients (which can include e.g., B, Cu, Mn, Fe, Cl, Mo, Zn, S) or traditional N—P—K fertilizers where the nitrogen, phosphorus, or potassium source is in an ionic form as well as other agro-chemicals (e.g., pesticides, herbicides, etc.) or macro-nutrients. In some embodiments, the fertilizer can be, for example, 10-34-0 (N—P—K), optionally including one or more of sulfur, boron and another micronutrient. In some cases, the nitrogen source is in the form of urea or an agriculturally acceptable urea salt. The fertilizer can include e.g., ammonium phosphate or ammonium thiosulphate.

In some embodiments, the formulations of the current disclosure were mixed with a concentrated/high salt solution. The exemplary procedure for a hard water test is as follows: Formulations described herein were mixed with different hard water standards, each with a different degree of hardness (e.g., CIPAC H standard water (in the example below: 634 ppm hardness, pH 6.0-7.0, $Ca^{2+}:Mg^{2+}=2.5:1$), CIPAC J standard water (6.34 ppm hardness, pH 6.0-7.0, $Ca^{2+}:Mg^{2+}=2.5:1$) and CIPAC G standard water (8000 ppm hardness, pH 6.0-7.0, $Mg^{2+}$)) at an active ingredient concentration of 200 ppm. In some embodiments, the formulations dispersed well and were stable for at least an hour, with no signs of the formation of flocs or sediments. In some embodiments, the formulation failed to disperse, formed flocs, sediments or other undesirable solids when diluted.

In some cases, the formulations of the present disclosure can be applied simultaneously with a high-salt solution or suspension such as a micronutrient solution, a fertilizer, pesticide, herbicide solution, or suspension (e.g., an in-furrow application, direct soil, and/or as a tank-mix mixture). The ability to mix and apply mectins and/or milbemycins with other agricultural ingredients such as liquid fertilizers is very useful to growers, as it reduces the number of required trips across crop fields and the expenditure of resources for application. In some cases, the formulations of the present disclosure may be mixed with liquid fertilizers of high ionic strength. In some cases the fertilizer is a 10-34-0 fertilizer, optionally including one or more of sulfur, boron and another micronutrient. In some cases, the nitrogen source is in the form of urea or an agriculturally acceptable urea salt. In some embodiments, the liquid fertilizer comprises a glyphosate or an agriculturally acceptable salt of glyphosate (e.g., ammonium, isopropylamine, dimethylamine or potassium salt). In some embodiments, the liquid fertilizer may be in the form of a solution or a suspension. In some embodiments, formulations of the present disclosure are stable when mixed with liquid fertilizers of increased or high ionic strength (e.g., at any of the ionic strengths described below). In some embodiments, when mixed with liquid fertilizers formulations of the current disclosure show no signs of sedimentation or flocculation.

Other potential additives that might be added into a spray tank that are charged and can decrease the stability of an agrochemical formulation include charged surfactants or polymers, inert ingredients such as urea, or other similar ingredients.

In some embodiments, the present disclosure provides compositions of a formulation of nanoparticles of polymer-associated active ingredients that are redispersible in solutions with high ionic strength. In some embodiments, the present disclosure also provides compositions of a formulation of nanoparticles of polymer-associated active ingredients that can be redispersed in water and then have a high salt solution or solid salt added and maintain their stability. In some embodiments, the formulations of the present disclosure are stable when dispersed in or dispersed in water and then mixed with solutions with ionic strength corresponding to $Ca^{2+}$ equivalents of about 0 to about 1 ppm, about 0 to about 10 ppm, about 0 to about 100 ppm, about 0 to about 342 ppm, about 0 to about 500 ppm, about 0 to about 1000 ppm, about 0 to about 5000 ppm, about 0 to about 8000 ppm, about 0 to about 10000 ppm, about 1 to about 10 ppm, about 1 to about 100 ppm, about 1 to about 342 ppm, about 1 to about 500 ppm, about 1 to about 1000 ppm, about 1 to about 5000 ppm, about 1 to about 8000 ppm, about 1 to about 10000 ppm, about 10 to about 100 ppm, about 10 to about 342 ppm, about 10 to about 500 ppm, about 10 to about 1000 ppm, about 10 to about 5000 ppm, about 10 to about 8000 ppm, about 10 to about 10000 ppm, about 100 to about 342 ppm, about 100 to about 500 ppm, about 100 to about 1000 ppm, about 100 to about 5000 ppm, about 100 to about 8000 ppm, about 100 to about 10000 ppm, about 342 to about 500 ppm, about 342 to about 1000 ppm, about 342 to about 5000 ppm, about 342 to about 8000 ppm, about 342 to about 10000 ppm, about 500 to about 1000 ppm, about 500 to about 5000 ppm, about 500 to about 8000 ppm, about 500 to about 10000 ppm, about 1000 to about 5000 ppm, about 1000 to about 8000 ppm, about 1000 to about 10000 ppm, about 5000 to about 8000 ppm, about 5000 to about 10000 ppm, about 8000 to about 10000 ppm.

Direct Soil & Seed Applications

In some embodiments, formulations of the current disclosure may be used to control pests by application to soil (inoculation of soil). The formulations of the current disclosure may be used to control pests via application to the soil in which a plant is to be planted prior to planting (i.e., as pre-plant incorporated application). In some embodiments, the formulations of the present disclosure are used to control pests via inoculation of the seed and soil at the time of seed planting (e.g., via an in-furrow application or T-banded application). The formulations of the current disclosure may also be applied to soil after planting but prior to emergence of the plant (i.e., as a pre-emergence application). In some embodiments, soil is inoculated with a formulation of the current disclosure via an aerosol spray or pouring.

In some embodiments, the mectin and milbemycin formulations of the current disclosure may be used to control pests in the aforementioned applications at an active ingredient use rate that is lower than the use rate listed on the labels of commercially available formulations of the same active ingredient, as described above. In some embodiments, a formulation of the present disclosure is used to control pests at an active ingredient use rate (or range of rates) that is less than about 75%, less than about 60%, less than about 50%, less than about 40%, less than about 30%, less than about 25%, less than about 20% or less than about 10% of a use rate listed on the labels of currently available commercial mectin and milbemycin products of the same active ingredient.

The formulations described here in can also be incorporated into seed treatments (also referred to as seed coatings or seed dressings). Seed treatments involve coating seeds with a pesticide and additional formulants, prior to planting. The seed, pesticide and formulants form a singular solid material. Generally, the seeds are individually coated, but some seeds may agglomerate during coating, and in some embodiments, this may be the desired result. Agglomerates of seeds can simplify planting and increase the likelihood of plant success because two or more seeds are delivered to one location.

Exemplary seed treatments can include any of the formulations described herein. In addition to the formulants described above in other application contexts, seed treatment formulations may also generally involve the use of dyes, thickeners, tackifiers, powdered minerals, binders/adhesives, additional polymers and other inert carriers. These various compounds are used in order to adhere the seed treatment formulation to the seed, allow it to be dried after fluid-based or fluidized process steps. The dyes used can be of particular importance because the colors can discourage birds from consuming the seeds. In some embodiments, seed treatments may include additional surfactants, soil amendment agents, plant amendment agents, water absorbents, oil absorbents, additional pesticides, plant growth promoters, fertilizers, macro- and/or micronutrients. These particular components change the chemistry of the seed environment, or soil environment near where the seed is planted. Because the formulations of the instant disclosure include a polymeric components it is possible, in some embodiments, that additional polymer(s), thickener(s) and/or inert carriers are not necessary to prepare an acceptable and effective seed coating. Furthermore, the formulants described above may result in the reduction of a particular seed treatment additive.

With respect to the polymer nanoparticle formulations described herein, in some embodiments, the formulation (e.g., HSLS or an SC) is prepared as described herein. The formulation is then mixed with the seed treatment components (i.e., the dye, the polymer, and any other components that will be in the coating on the seeds). This mixture is then sprayed through a fluidized bed with the seeds to coat the seeds. After the coating, the coated seeds are dried and generally ready for use. Any type of particulate coating technology may be used, as the coating method is not limited to just fluidized bed coating techniques. For example, rotary coaters (e.g., rotary pelleting), film coating, pan coating, tumbling drums, and agglomerators may all be used in coating seeds with the formulations.

In some embodiments, the mectin and milbemycin formulations of the current disclosure can be used to control pests when applied to seeds. In some embodiments, the formulations of the current disclosure are used to control pests when applied to seeds at an active ingredient use rate that is less than the use rate of commercially available formulations of the same active ingredient when applied to seeds. In some embodiments, a formulation of the present disclosure is used to control pests when applied to seeds at an active ingredient use rate that is less than about 75%, less than about 60%, less than about 50%, less than about 40%, less than about 30%, less than about 25%, less than about 20% or less than about 10%, of a use rate listed on the label of a currently available commercial mectin or milbemycin product of the same active ingredient.

EXAMPLES

Notes and Abbreviations

Abamectin: technical grade, 92.9% purity (by weight)

Proxel™ BD-20: biocide, 19.3 weight % active biocide ingredient (1,2-benzisothiazolin-3-one), Arch Chemicals Inc.

Trans 10-A: Antifoaming agent, 10% Silicone Antifoam Emulsion, Water-based, 10 wt. % polydimethylsiloxane compound, Trans-Chemco, Inc.

RO water: water purified via reverse osmosis; DMF: N,N-dimethyl-formamide

Monomer Abbreviations—MAA: methacrylic acid; EA: ethyl acrylate; S: styrene; NaAMPS: sodium acrylamido-2-methylpropanesulfonate.

Particle sizes were measured via DLS using a Malvern Zetasizer ZS. In relevant sections of the examples, formulations and static binding assays employed a Vortex Genie™ 2 (Scientific Industries) equipped with a multi-tube holder. Active ingredient content was determined by HPLC-UV analysis.

I: Nanoparticle Preparation

Example 1

Preparation of Polymer Nanoparticles from Poly(S-MAA-NaAMPS) [25-20-55 Weight Ratio of Input Monomers]

Into a 500 mL 3-neck round bottom flask (reactor) were weighed 110 g of Lubrizol 2403 (50 wt. % NaAMPS in water), 25 g of styrene, 20 g of MAA and 115 g of DMF (ACS reagent grade). The resulting solution was yellowish in color. The reactor was fitted with a mechanical stirrer, a condenser, and a rubber septum. 0.2 g of Vazo 88 [1,1'-azobis(cyclohexanecarbonitrile)] was dissolved in 10 mL of DMF (ACS reagent grade) in a 20 mL scintillation vial, which was then sealed with a rubber septum. A gentle flow of $N_2$ was used to purge the contents of both the 500 mL flask and vial for 15 hours. The flask was then heated to 100° C. in a pre-heated oil bath for 10 min with mechanical stirring at 210 rpm. The Vazo 88 solution was transferred to the reactor via a double tipped needle. The resultant solution was yellowish. The reactor was maintained at 100° C. and continuously stirred at 250 rpm for 20 h after which time the reaction mixture appeared hazy, with noticeably increased viscosity. The reactor was cooled to room temperature. At room temperature, the mixture appeared hazier and more viscous (Viscosity=20.2 P at 25.4 C).

The polymer was isolated via precipitation in isopropanol according to the following procedure: Into a 4 L glass beaker equipped with a stir bar was weighed 1576 g of isopropanol. The reaction mixture was added dropwise to the isopropanol with continuous stirring over the course of about 30 minutes, leading to the formation of white precipitates. After the addition was complete, the isopropanol mixture was allowed to stir for an hour. After the stirring was stopped, the precipitate was allowed to settle for 30 minutes and most (about 80%) of the isopropanol was decanted. The remaining isopropanol and precipitate were transferred to plastic bottles and centrifuged for 5 minutes at 3400 rpm on a Beckman GS-6R centrifuge. The supernatants were decanted and the plastic bottles were placed in a vacuum oven at 60° C. for 6 hours to dry the precipitate, yielding 73.8 g of a white solid (73.8% yield).

The isolated polymer was used to prepare nanoparticles according to the following procedure: 61.5 g of the copolymer was added to 3 L of RO water (the pH of the dispersion was 5.8). At this pH, the polymer did not completely dissolve. After stirring overnight, the pH was adjusted to 7.50 via the dropwise addition of 6 N NaOH to provide a clear solution. Into a 4 L glass beaker equipped with a stir bar were added 1.0 L of the solution of copolymer and 2.56 L RO water. The pH of this solution was 7.98. The polymer dissolved completely at this pH, yielding a solution with a viscosity of 2.65 cP at 25.2° C. 44.5 g of solid NaCl was added to the polymer solution, which was stirred until all of the NaCl had completely dissolved. After the addition of NaCl, the pH decreased to 7.14, and the viscosity decreased to 1.23 cP at 24.8° C. The solution was transferred to two 2 L re-crystallization dishes equipped with stir bars and exposed to four 254 nm UV germicidal lamps (G25T8) for 8 hours with constant stirring, producing a yellowish dispersion. Upon acidification to pH 3 with 6N HCl, the dispersion remained clear with no precipitation. The dispersion was transferred to dialysis bags (Mw cut-off=12-14 KDa, about 600 mL/bag) and dialyzed against RO water at pH 2.5-3.0 twice (~20 L of RO water per bag, 20 h for each dialysis cycle). The dispersions were freeze-dried to provide 14.65 g of polymer nanoparticles (71.5% yield).

Example 2

Preparation of Polymer Nanoparticles from Poly(S-MAA-NaAMPS), 30-10-60 Weight Ratio of Input Monomers Into a two-necked 150 mL round bottom flask (reactor) equipped with a stir bar were weighed 12 g of solid NaAMPS and 90 g of DMF. Into a 20 mL glass scintillation vial were weighed 6 g of styrene and 2 g of MAA, which were then transferred to the flask. The flask was fitted with a condenser and a rubber septum. Into a separate 20 mL glass scintillation vial were weighed 0.2 g of Vazo 88 [1,1'-azobis(cyclohexanecarbonitrile)] and 10 g of DMF. A gentle flow of $N_2$ was used to purge the contents of both the 150 mL flask and 20 mL vial for 6 hours.

The 150 mL flask was heated to 100° C. in an oil bath. The Vazo 88 solution was transferred to the flask via a double tipped needle. The flask was maintained at 100° C. and continuously stirred for approximately 20 hours.

The polymer was isolated via precipitation in isopropanol according to the following procedure: Into a 4 L glass beaker equipped with a stir bar was weighed about 791 g of isopropanol. The reaction mixture was added dropwise to the isopropanol with continuous stirring over the course of about 30 minutes, leading to the formation of precipitates. After the addition was complete, the isopropanol mixture was allowed to stir for 30 minutes. The stirring was stopped, the precipitate was allowed to settle, and most (about 80%) of the isopropanol was decanted. The remaining isopropanol and precipitate were transferred to plastic bottles and centrifuged for 5 minutes at 3400 rpm on a Beckman GS-6R centrifuge. The supernatants were decanted and the plastic bottles were vacuum dried at elevated temperature in a vacuum oven for 3 hours to provide 12.2 g of a white solid (60.9% yield).

The isolated polymer was used to prepare nanoparticles according to the following procedure: Into a 1 L glass beaker equipped with a stir bar were added 8.0 g of the copolymer and 1 L RO water (pH=6.15). The pH was adjusted to 10.0 via the addition of ~1 mL of 6N NaOH and the contents were stirred overnight to provide a clear solution (the pH after stirring overnight was 9.3). 17.5 g of NaCl were added to the solution and the pH decreased to 8.94. The dispersion was transferred to a 2 L re-crystallization dish equipped with a stir bar and exposed to four 254 nm UV germicidal lamps (G25T8) for 2 hours with constant stirring. The resulting dispersion was acidified to pH 2.90 via the addition of 6N HCl and transferred to dialysis bags (Mw cut-off=12-14 KDa, about 500 mL/bag), which were placed in a 25 L bucket and dialyzed against RO water at pH 3 twice (about 22.5 L of water and 20 h for each dialysis cycle). The dispersion was freeze-dried (from liquid $N_2$) to provide 6.37 g of polymer nanoparticles (79.4% yield).

II: Formulations

Example 3

Preparation of a HSLS Formulation of Nanoparticles or Aggregates of Nanoparticles of Polymer-Associated Abamectin Via Ball-Milling [Nanoparticles Derived from p(S-MAA-NaAMPS); 5:1 Ratio of Abamectin:Nanoparticles]

A formulation targeting an active ingredient loading of 10.0% was prepared according to the following procedure: To a 20 mL glass scintillation vial were added 1.6324 g of Abamectin (technical grade), 3.0014 g of a 10 wt. % aqueous dispersion of p(S-MAA-NaAMPS) nanoparticles of Example 1, 0.1501 g of Geropon® T-77, 0.2994 g of Geropon® TA/72, 0.1513 g of Atlox™ 4913, 0.7579 g of 1,2-propanediol, 0.6042 g of Trans 10-A, 0.0475 g of Proxel™ BD-20, 0.0148 g of 2-hydroxy-4-n-octyloxy benzophenone (UV-blocker) and 8.3852 g of RO water. 30 g of stainless steel shots (600-800 μm) were added to the vial, which was sealed, secured to a vortex and shaken on setting 6 for 3 days. The formulation was isolated from the steel shots via pipette.

When the formulation was dispersed in CIPAC D water at 200 ppm Abamectin, the Z-ave particle size was found to be 185 nm with a polydispersity index of 0.155. When the formulation was dispersed in CIPAC D water at 40 ppm Abamectin, the Z-ave particle size was found to be 183 nm with a polydispersity index of 0.165. The active ingredient assay indicated that the formulation contained 10.0% Abamectin.

Example 4

Preparation of a HSLS Formulation of Nanoparticles or Aggregates of Nanoparticles of Polymer-Associated Abamectin Via Ball-Milling [Nanoparticles Derived from p(MAA-co-S); 1:1 Ratio of Abamectin:Nanoparticles]

A formulation targeting an active ingredient loading of 2% was prepared according to the following procedure: To a 20 mL glass scintillation vial were added 0.3233 g of Abamectin (technical grade), 3.0253 g of a 10 wt. % aqueous dispersion of nanoparticles derived from poly(MAA-co-S) [MAA:S ratio=approximately 75:25 by weight], 0.1500 g of Geropon® T-77, 0.3052 g of Geropon® TA/72, 0.1581 g of Atlox™ 4913, 0.7524 g of 1,2-propanediol, 0.5888 g of Trans 10-A, 0.0463 g of Proxel™ BD-20, 0.0167 g of 2-hydroxy-4-n-octyloxy benzophenone (UV-blocker) and 9.7366 g of RO water. 30 g of stainless steel shots (600-800 μm) were added to the vial, which was sealed, secured to a vortex and shaken on setting 6 for 2 days. The formulation was isolated from the steel shots via pipette.

When the formulation was dispersed in CIPAC D water at 40 ppm Abamectin, the Z-ave particle size was found to be 173 nm with a polydispersity index of 0.169. The active ingredient assay indicated that the formulation contained 1.8% Abamectin.

Example 5

Preparation of a HSLS Formulation of Nanoparticles or Aggregates of Nanoparticles of Polymer-Associated Abamectin Via Ball-Milling [Nanoparticles Derived from p(MAA-co-S); 1:1 Ratio of Abamectin:Nanoparticles]

A formulation targeting an active ingredient loading of 4.1% was prepared according to the following procedure: To a 20 mL glass scintillation vial were added 0.6621 g of Abamectin (technical grade), 6.0294 g of a 10 wt. % aqueous dispersion of nanoparticles derived from poly(MAA-co-S) [MAA:S ratio=approximately 75:25 by weight], 0.1565 g of Geropon® T-77, 0.3012 g of Geropon® TA/72, 0.1590 g of Atlox™ 4913, 0.7846 g of 1,2-propanediol, 0.5892 g of Trans 10-A, 0.0512 g of Proxel™ BD-20, 0.0139 g of 2-hydroxy-4-n-octyloxy benzophenone (UV-blocker) and 6.3522 g of RO water. 30 g of stainless steel shots (600-800 μm) were added to the vial, which was sealed, secured to a vortex and shaken on setting 6 for 2 days. The formulation was isolated from the steel shots via pipette.

When the formulation was dispersed in CIPAC D water at 40 ppm Abamectin, the Z-ave particle size was found to be 170 nm with a polydispersity index of 0.161. The active ingredient assay indicated that the formulation contained 3.5% Abamectin.

Example 6

Preparation of a HSLS Formulation of Nanoparticles or Aggregates of Nanoparticles of Polymer-Associated Abamectin Via Ball-Milling [Nanoparticles Derived from p(MAA-co-S); 1:2 Ratio of Abamectin:Nanoparticles]

A formulation targeting an active ingredient loading of 2.1% was prepared according to the following procedure: To a 20 mL glass scintillation vial were added 0.3403 of Abamectin (technical grade), 5.9964 g of a 10 wt. % aqueous dispersion of nanoparticles derived from poly(MAA-co-S) [MAA:S ratio=approximately 75:25 by weight], 0.1549 g of Geropon® T-77, 0.3029 g of Geropon® TA/72, 0.1556 g of Atlox™ 4913, 0.7654 g of 1,2-propanediol, 0.5931 g of Trans 10-A, 0.0417 g of Proxel™ BD-20, 0.0146 g of 2-hydroxy-4-n-octyloxy benzophenone (UV-blocker) and 6.6459 g of RO water. 30 g of stainless steel shots (600-800 μm) were added to the vial, which was sealed, secured to a vortex and shaken on setting 6 for 2 days. The formulation was isolated from the steel shots via pipette.

When the formulation was dispersed in CIPAC D water at 40 ppm Abamectin, the Z-ave particle size was found to be 190 nm with a polydispersity index of 0.209. The active ingredient assay indicated that the formulation contained 1.8% Abamectin.

Example 7

Preparation of a HSLS Formulation of Nanoparticles or Aggregates of Nanoparticles of Polymer-Associated Abamectin Via Ball-Milling [Nanoparticles Derived from p(S-MAA-NaAMPS); 1:1 Ratio of Abamectin:Nanoparticles]

A formulation targeting an active ingredient loading of 4% was prepared according to the following procedure: To a 20 mL glass scintillation vial were added 0.6530 g of Abamectin (technical grade), 6.0383 g of a 10 wt. % aqueous dispersion of p(S-MAA-NaAMPS) nanoparticles of Example 1, 0.1530 g of Geropon® T-77, 0.2940 g of Geropon® TA/72, 0.1669 g of Atlox™ 4913, 0.7514 g of 1,2-propanediol, 0.6085 g of Trans 10-A, 0.0505 g of Proxel™ BD-20, 0.0149 g of 2-hydroxy-4-n-octyloxy benzophenone (UV-blocker) and 6.4188 g of RO water. 30 g of stainless steel shots (600-800 μm) were added to the vial, which was sealed, secured to a vortex and shaken on setting 6 for 2 days. The formulation was isolated from the steel shots via pipette.

When the formulation was dispersed in CIPAC D water at 40 ppm Abamectin, the Z-ave particle size was found to be 169 nm with a polydispersity index of 0.160. The active ingredient assay indicated that the formulation contained 4.0% Abamectin.

Example 8

Preparation of a HSLS Formulation of Nanoparticles or Aggregates of Nanoparticles of Polymer-Associated Abamectin Via Ball-Milling [Nanoparticles Derived from p(S-MAA-NaAMPS); 1:2 Ratio of Abamectin:Nanoparticles]

A formulation targeting an active ingredient loading of 4.0% was prepared according to the following procedure: To a 20 mL glass scintillation vial were added 0.6580 g of Abamectin (technical grade), 12.0190 g of a 10 wt. % aqueous dispersion of p(S-MAA-NaAMPS) nanoparticles of Example 1, 0.1511 g of Geropon® T-77, 0.3036 g of Geropon® TA/72, 0.1602 g of Atlox™ 4913, 0.7515 g of 1,2-propanediol, 0.6234 g of Trans 10-A, 0.0526 g of Proxel™ BD-20, 0.0137 g of 2-hydroxy-4-n-octyloxy benzophenone (UV-blocker) and 0.4331 g of RO water. 30 g of stainless steel shots (600-800 µm) were added to the vial, which was sealed, secured to a vortex and shaken on setting 6 for 2 days. The formulation was isolated from the steel shots via pipette.

When the formulation was dispersed in CIPAC D water at 40 ppm Abamectin, the Z-ave particle size was found to be 291 nm with a polydispersity index of 0.253. The active ingredient assay indicated that the formulation contained 3.6% Abamectin.

Example 9

Preparation of a HSLS Formulation of Nanoparticles or Aggregates of Nanoparticles of Polymer-Associated Abamectin Via Ball-Milling [Nanoparticles Derived from p(S-MAA-NaAMPS); 1:1 Ratio of Abamectin:Nanoparticles]

A formulation targeting an active ingredient loading of 2.1% was prepared according to the following procedure: To a 20 mL glass scintillation vial were added 0.3461 g of Abamectin (technical grade), 0.2962 g of the p(S-MAA-NaAMPS) nanoparticles of Example 2, 0.1518 g of Geropon® T-77, 0.2938 g of Geropon® TA/72, 0.1541 g of Atlox™ 4913, 0.7661 g of 1,2-propanediol, 0.6036 g of Trans 10-A, 0.0450 g of Proxel™ BD-20, 0.0225 g of 2-hydroxy-4-n-octyloxy benzophenone (UV-blocker) and 12.4079 g of RO water. 30 g of stainless steel shots (600-800 µm) were added to the vial, which was sealed, secured to a vortex and shaken on setting 6 for 2 days. The formulation was isolated from the steel shots via pipette.

When the formulation was dispersed in CIPAC D water at 40 ppm Abamectin, the Z-ave particle size was found to be 172 nm with a polydispersity index of 0.119. The active ingredient assay indicated that the formulation contained 2.0% Abamectin.

III: Static Soil Adsorption Studies

Example 10

Static Soil Adsorption Assays with Abamectin Formulation of the Current Disclosure The following static soil binding assay was performed to determine the soil adsorption characteristics of formulations prepared according to the current disclosure. The mobility of an active in a soil column is related to its soil binding and adsorption characteristics, and formulations that reduce or prevent the binding or adsorption of active ingredients to soil can impart enhanced soil mobility properties to the active. The assay employed silt loam type soil (30.9% sand, 51.7% silt, 17.4% clay; 2.12% organic carbon; pH ($CaCl_2$) 7.1). The soil was sieved through a No. 10 mesh sieve and allowed to air dry prior to use in the assays.

Exemplary procedure for static assays: 2.00 g of soil and 18 mL of 10 mM $CaCl_2$ were added to a 30 mL glass centrifugation tube (KIMAX® Heavy-Duty Round-Bottom Centrifuge Tube with Screw Caps, Kimble Chase). The tube was secured to a vortex and shaken on setting 3 for about 1 day. 2 mL of a stock dispersion with a concentration of 400 ppm prepared from one of the formulations described above in Example 3-Example 9 was then added to the tube, which was sealed and shaken for about 24 hours. The entire glass tube was then placed and secured in a 50 mL plastic centrifugation tube and centrifuged on a Beckman GS-6R centrifuge at 900 rpm for 3 minutes. To determine the supernatant Abamectin content, a 1 mL aliquot the supernatant was carefully withdrawn via pipette and placed in a 20 mL glass scintillation vial. 4 mL of HPLC grade acetonitrile was added to the vial, which was then shaken on a vortex for about 30 minutes. The liquid was filtered through Econofilter 25 (0.2 µM rC, Agilent Technologies) and analyzed via HPLC-UV. Each static soil binding assay was performed in triplicate. A control sample with no soil was subjected to the same procedure. The percent of Abamectin in the supernatant is calculated from the ratio of Abamectin found in the supernatant of the soil samples and the control sample (no soil).

Static adsorption assays with the formulations of Examples 3-9 were performed via procedures analogous to the representative procedure outlined above. The outcomes are given in Table 3.

TABLE 3

| Formulation | Abamectin supernatant content of no soil control (ppm) | Abamectin supernatant content after soil binding assay (ppm) | % Abamectin in Supernatant (based on control) |
|---|---|---|---|
| Example 3 | 36.8 | 2.5 | 7 |
| Example 4 | 41.4 | 0.2 | <1 |
| Example 5 | 39.7 | 0.2 | <1 |
| Example 6 | 45.5 | 1.0 | 2 |
| Example 7 | 40.9 | 3.5 | 9 |
| Example 8 | 40.3 | 7.6 | 19 |
| Example 9 | 40.6 | 3.8 | 9 |

As can be seen, the Abamectin formulations of the current disclosure, particularly the formulation of Example 8, maintained a fraction of Abamectin in the supernatant with centrifugation in the presence of soil.

The invention claimed is:

1. A formulation comprising:
   a nanoparticle comprising a polymer-associated mectin, milbemycin or spinosyn compound with an average diameter of between about 1 nm and about 500 nm; wherein the polymer is a polyelectrolyte;
   between about 0.5 weight percent and about 5 weight percent of an ethoxylated tridecyl alcohol dispersant;
   between about 0.5 weight percent and about 5 weight percent of a sodium dodecylbenzene sulfonate wetting agent;
   between about 0.1 weight percent and about 1 weight percent of an anti-foaming agent;
   between about 0.01 weight percent and about 0.2 weight percent of a preservative; and
   water.

2. The formulation of claim 1, wherein the ratio of mectin or milbemycin compound to polymer within the nanoparticles is between about 5:1 and about 1:5.

3. The formulation of claim 1, wherein the polymer is selected from the group consisting of poly(methacrylic acid co-ethyl acrylate), poly(methacrylic acid-co-styrene); poly(methacrylic acid-co-butylmethacrylate), poly[acrylic acid-co-poly(ethylene glycol)methyl ether methacrylate], poly(n-butylmethacrylate-co-methacrylic acid), poly(acrylic acid-co-styrene), and poly(methacrylic acid-co-styrene-co-sodium acrylamide-2-methylpropanesulfonate).

4. The formulation of claim 1, wherein the polymer is a random copolymer.

5. The formulation of claim 1, wherein the formulation is in the form of a high solids liquid suspension or a suspension concentrate.

6. The formulation of claim 1 further comprising between about 0.05 weight % and about 5 weight % of a thickener.

7. The formulation of claim 1 further comprising between about 5 weight % and about 10 weight % of an anti-freezing agent.

8. The formulation of claim 1, wherein the polymer-associated mectin, milbemycin or spinosyn compound is between about 5 weight % and about 40 weight % of the formulation.

9. The formulation of claim 1, further comprising between about 1 weight % and about 20 weight % of a non-ionic surfactant.

10. The formulation of claim 1, further comprising a fungicide and/or a pesticide.

11. A method of using the formulation of claim 1 comprising the steps of:
applying the formulation to a plant.

* * * * *